(12) United States Patent
Allison

(10) Patent No.: US 8,603,073 B2
(45) Date of Patent: Dec. 10, 2013

(54) SYSTEMS AND METHODS WITH INTERRUPT/RESUME CAPABILITIES FOR TREATING SUBCUTANEOUS LIPID-RICH CELLS

(75) Inventor: John W. Allison, Los Altos, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 986 days.

(21) Appl. No.: 12/337,544

(22) Filed: Dec. 17, 2008

(65) Prior Publication Data
US 2010/0152824 A1 Jun. 17, 2010

(51) Int. Cl.
*A61M 1/00* (2006.01)

(52) U.S. Cl.
USPC ........................................................ 604/542

(58) Field of Classification Search
USPC ............ 604/542, 291; 606/20–26; 607/96–99
See application file for complete search history.

(56) References Cited

U.S. PATENT DOCUMENTS

| | | |
|---|---|---|
| 681,806 A | 9/1901 | Mignault |
| 889,810 A | 6/1908 | Robinson |
| 2,516,491 A | 7/1950 | Swastek |
| 2,766,619 A | 10/1956 | Tribus et al. |
| 3,093,135 A | 6/1963 | Hirschhorn |
| 3,132,688 A | 5/1964 | Nowak |
| 3,282,267 A | 11/1966 | Wiliam |
| 3,502,080 A | 3/1970 | Hirschhorn |
| 3,587,577 A | 6/1971 | Smirnov et al. |
| 3,591,645 A | 7/1971 | Selwitz |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Stumpf et al. |
| 3,942,519 A | 3/1976 | Shock |
| 3,948,269 A | 4/1976 | Zimmer |
| 3,986,385 A | 10/1976 | Johnston et al. |
| 4,002,221 A | 1/1977 | Buchalter |
| 4,140,130 A | 2/1979 | Storm, III |
| 4,178,429 A | 12/1979 | Scheffer |
| 4,202,336 A | 5/1980 | van Gerven et al. |
| 4,266,043 A | 5/1981 | Fujii et al. |
| 4,381,009 A | 4/1983 | Del Bon et al. |
| 4,396,011 A | 8/1983 | Mack et al. |
| 4,483,341 A | 11/1984 | Witteles |
| 4,528,979 A | 7/1985 | Marchenko et al. |
| 4,531,524 A | 7/1985 | Mioduski |

(Continued)

FOREIGN PATENT DOCUMENTS

| | | |
|---|---|---|
| CN | 1511503 | 7/2004 |
| CN | 1741777 | 3/2006 |

(Continued)

OTHER PUBLICATIONS

U.S. Appl. No. 12/196,246, filed Aug. 21, 2008, Levinson.

(Continued)

*Primary Examiner* — Theodore J Stigell
*Assistant Examiner* — Diva K Chander
(74) *Attorney, Agent, or Firm* — Perkins Coie, LLP

(57) ABSTRACT

Systems for removing heat from a subject's subcutaneous lipid-rich regions, such as tissue, organs, cells, and so forth, are described herein. In various embodiments, the system includes a treatment device and a controller for controlling a treatment process. The controller is configured to detect and compensate for an interruption in the treatment process.

21 Claims, 8 Drawing Sheets

(56) References Cited

U.S. PATENT DOCUMENTS

| | | |
|---|---|---|
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt et al. |
| 4,741,338 A | 5/1988 | Miyamae et al. |
| 4,764,463 A | 8/1988 | Mason et al. |
| 4,802,475 A | 2/1989 | Weshahy et al. |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,906,463 A | 3/1990 | Cleary et al. |
| 4,930,317 A | 6/1990 | Klein |
| 4,935,345 A | 6/1990 | Guibeau et al. |
| 4,961,422 A | 10/1990 | Marchosky et al. |
| 4,962,761 A | 10/1990 | Golden |
| 4,990,144 A | 2/1991 | Blott |
| 5,007,433 A | 4/1991 | Hermsdorffer et al. |
| 5,018,521 A | 5/1991 | Campbell |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen et al. |
| 5,143,063 A | 9/1992 | Fellner |
| 5,148,804 A | 9/1992 | Hill et al. |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney |
| 5,330,745 A | 7/1994 | McDow |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold |
| 5,351,677 A | 10/1994 | Kami et al. |
| 5,362,966 A | 11/1994 | Rosenthal et al. |
| 5,427,772 A | 6/1995 | Hagan |
| 5,433,717 A | 7/1995 | Rubinsky et al. |
| 5,456,703 A | 10/1995 | Beeuwkes, III |
| 5,472,416 A | 12/1995 | Blugerman et al. |
| 5,497,596 A | 3/1996 | Zatkulak |
| 5,505,726 A | 4/1996 | Meserol |
| 5,505,730 A | 4/1996 | Edwards |
| 5,507,790 A | 4/1996 | Weiss et al. |
| 5,514,105 A | 5/1996 | Goodman, Jr. et al. |
| 5,514,170 A | 5/1996 | Mauch |
| 5,531,742 A | 7/1996 | Barken |
| 5,562,604 A | 10/1996 | Yablon et al. |
| 5,571,801 A | 11/1996 | Segall et al. |
| 5,603,221 A | 2/1997 | Maytal et al. |
| 5,628,769 A | 5/1997 | Saringer et al. |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay |
| 5,660,836 A | 8/1997 | Knowlton |
| 5,672,172 A | 9/1997 | Zupkas |
| 5,733,280 A | 3/1998 | Avitall |
| 5,741,248 A | 4/1998 | Stern et al. |
| 5,746,736 A | 5/1998 | Tankovich |
| 5,755,663 A | 5/1998 | Larsen et al. |
| 5,755,753 A | 5/1998 | Knowlton |
| 5,759,182 A | 6/1998 | Varney et al. |
| 5,759,764 A | 6/1998 | Polovina |
| 5,769,879 A | 6/1998 | Richards et al. |
| 5,785,955 A | 7/1998 | Fischer |
| 5,817,050 A | 10/1998 | Klein |
| 5,830,208 A | 11/1998 | Muller |
| 5,833,685 A | 11/1998 | Tortal et al. |
| 5,844,013 A | 12/1998 | Kenndoff et al. |
| 5,871,524 A | 2/1999 | Knowlton |
| 5,871,526 A | 2/1999 | Gibbs et al. |
| 5,895,418 A | 4/1999 | Saringer et al. |
| 5,901,707 A | 5/1999 | Goncalves et al. |
| 5,902,256 A | 5/1999 | Benaron |
| 5,919,219 A | 7/1999 | Knowlton |
| 5,944,748 A | 8/1999 | Mager et al. |
| 5,948,011 A | 9/1999 | Knowlton |
| 5,964,092 A | 10/1999 | Tozuka et al. |
| 5,964,749 A | 10/1999 | Eckhouse et al. |
| 5,967,976 A | 10/1999 | Larsen et al. |
| 5,986,167 A | 11/1999 | Arteman et al. |
| 6,017,337 A | 1/2000 | Pira et al. |
| 6,023,932 A | 2/2000 | Johnston et al. |
| 6,032,675 A | 3/2000 | Rubinsky |
| 6,039,694 A | 3/2000 | Larson et al. |
| 6,041,787 A | 3/2000 | Rubinsky |
| 6,049,927 A | 4/2000 | Thomas et al. |
| 6,051,159 A | 4/2000 | Hao et al. |
| 6,074,415 A | 6/2000 | Der Ovanesian |
| 6,093,230 A | 7/2000 | Johnson, III et al. |
| 6,102,885 A | 8/2000 | Bass |
| 6,120,519 A | 9/2000 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,494,844 B1 | 12/2002 | Van Bladel et al. |
| 6,519,964 B2 | 2/2003 | Bieberich |
| 6,523,354 B1 | 2/2003 | Tolbert |
| 6,527,765 B2 | 3/2003 | Kelman et al. |
| 6,544,248 B1 | 4/2003 | Bass |
| 6,548,297 B1 | 4/2003 | Kuri-Harcuch et al. |
| 6,551,255 B2 | 4/2003 | Van Bladel et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,592,577 B2 | 7/2003 | Abboud et al. |
| 6,605,080 B1 | 8/2003 | Altshuler et al. |
| 6,626,854 B2 | 9/2003 | Friedman et al. |
| 6,635,053 B1 | 10/2003 | Lalonde et al. |
| 6,645,162 B2 | 11/2003 | Friedman et al. |
| 6,645,229 B2 | 11/2003 | Matsumura et al. |
| 6,648,904 B2 | 11/2003 | Altshuler et al. |
| 6,699,266 B2 | 3/2004 | Lachenbruch et al. |
| 6,718,785 B2 | 4/2004 | Bieberich |
| 6,741,895 B1 | 5/2004 | Gafni et al. |
| 6,746,474 B2 | 6/2004 | Saadat |
| 6,749,624 B2 | 6/2004 | Knowlton |
| 6,764,502 B2 | 7/2004 | Bieberich |

(56) References Cited

U.S. PATENT DOCUMENTS

| | | |
|---|---|---|
| 6,789,545 B2 | 9/2004 | Littrup et al. |
| 6,820,961 B2 | 11/2004 | Johnson |
| 6,821,274 B2 | 11/2004 | McHale et al. |
| 6,840,955 B2 | 1/2005 | Ein |
| 6,878,144 B2 | 4/2005 | Altshuler et al. |
| 6,904,956 B2 | 6/2005 | Noel |
| 6,918,903 B2 | 7/2005 | Bass |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 7,005,558 B1 | 2/2006 | Johansson et al. |
| 7,022,121 B2 | 4/2006 | Stern et al. |
| 7,037,326 B2 | 5/2006 | Lee et al. |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,258,674 B2 | 8/2007 | Cribbs et al. |
| 7,347,855 B2 | 3/2008 | Eshel et al. |
| 7,367,341 B2 | 5/2008 | Anderson et al. |
| 7,713,266 B2 | 5/2010 | Elkins et al. |
| 7,854,754 B2 | 12/2010 | Ting et al. |
| 8,192,474 B2 * | 6/2012 | Levinson ................. 607/96 |
| 2001/0031459 A1 | 10/2001 | Fahy et al. |
| 2001/0039439 A1 | 11/2001 | Elkins et al. |
| 2001/0045104 A1 | 11/2001 | Bailey et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0103520 A1 | 8/2002 | Latham |
| 2002/0117293 A1 | 8/2002 | Campbell |
| 2002/0120315 A1 | 8/2002 | Furuno et al. |
| 2002/0151887 A1 | 10/2002 | Stern et al. |
| 2002/0188286 A1 | 12/2002 | Quijano et al. |
| 2003/0044764 A1 | 3/2003 | Soane et al. |
| 2003/0055414 A1 | 3/2003 | Altshuler et al. |
| 2003/0069618 A1 | 4/2003 | Smith et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0125649 A1 | 7/2003 | McIntosh et al. |
| 2003/0199226 A1 | 10/2003 | Sommer et al. |
| 2003/0220674 A1 | 11/2003 | Anderson et al. |
| 2003/0236487 A1 | 12/2003 | Knowlton |
| 2004/0006328 A1 | 1/2004 | Anderson |
| 2004/0009936 A1 | 1/2004 | Tang et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 | 4/2004 | Altshuler et al. |
| 2004/0074629 A1 | 4/2004 | Noel |
| 2004/0093042 A1 | 5/2004 | Altshuler et al. |
| 2004/0104012 A1 | 6/2004 | Zhou et al. |
| 2004/0162596 A1 | 8/2004 | Altshuler et al. |
| 2004/0176667 A1 | 9/2004 | Mihai et al. |
| 2004/0199226 A1 | 10/2004 | Shadduck |
| 2004/0210214 A1 | 10/2004 | Knowlton |
| 2004/0210287 A1 | 10/2004 | Greene |
| 2004/0215294 A1 | 10/2004 | Littrup et al. |
| 2004/0259855 A1 | 12/2004 | Anderson et al. |
| 2005/0049661 A1 | 3/2005 | Koffroth |
| 2005/0154431 A1 | 7/2005 | Quistgaard et al. |
| 2005/0159986 A1 | 7/2005 | Breeland et al. |
| 2005/0182462 A1 | 8/2005 | Chornenky et al. |
| 2005/0187597 A1 | 8/2005 | Vanderschuit |
| 2005/0222565 A1 | 10/2005 | Manstein |
| 2005/0251120 A1 | 11/2005 | Anderson et al. |
| 2005/0261753 A1 | 11/2005 | Littrup et al. |
| 2005/0283144 A1 | 12/2005 | Shiono et al. |
| 2006/0030778 A1 | 2/2006 | Mendlein et al. |
| 2006/0036300 A1 | 2/2006 | Kreindel |
| 2006/0074313 A1 | 4/2006 | Slayton et al. |
| 2006/0079852 A1 | 4/2006 | Bubb et al. |
| 2006/0122509 A1 | 6/2006 | Desilets |
| 2006/0200063 A1 | 9/2006 | Munro et al. |
| 2006/0234899 A1 | 10/2006 | Nekmard et al. |
| 2006/0270745 A1 | 11/2006 | Hunt et al. |
| 2006/0293734 A1 | 12/2006 | Scott et al. |
| 2007/0010861 A1 * | 1/2007 | Anderson et al. ............... 607/96 |
| 2007/0032561 A1 | 2/2007 | Lin et al. |
| 2007/0055173 A1 | 3/2007 | DeLonzor et al. |
| 2007/0129714 A1 | 6/2007 | Elkins et al. |
| 2007/0141265 A1 | 6/2007 | Thomson |
| 2007/0198071 A1 | 8/2007 | Ting et al. |
| 2007/0239075 A1 | 10/2007 | Rosenberg et al. |
| 2007/0249519 A1 | 10/2007 | Guha et al. |
| 2007/0255187 A1 | 11/2007 | Branch |
| 2007/0255362 A1 | 11/2007 | Levinson et al. |
| 2007/0270925 A1 | 11/2007 | Levinson |
| 2007/0282249 A1 | 12/2007 | Quisenberry et al. |
| 2008/0046047 A1 | 2/2008 | Jacobs |
| 2008/0077201 A1 | 3/2008 | Levinson et al. |
| 2008/0077202 A1 * | 3/2008 | Levinson ................. 607/96 |
| 2008/0077211 A1 | 3/2008 | Levinson et al. |
| 2008/0140371 A1 | 6/2008 | Warner |
| 2008/0183164 A1 | 7/2008 | Elkins et al. |
| 2008/0287839 A1 | 11/2008 | Rosen et al. |
| 2009/0018623 A1 * | 1/2009 | Levinson et al. ............... 607/96 |
| 2009/0018624 A1 * | 1/2009 | Levinson et al. ............... 607/96 |
| 2009/0018625 A1 * | 1/2009 | Levinson et al. ............... 607/96 |
| 2009/0018626 A1 * | 1/2009 | Levinson et al. ............... 607/96 |
| 2009/0018627 A1 * | 1/2009 | Levinson et al. ............... 607/96 |
| 2009/0118722 A1 | 5/2009 | Ebbers et al. |
| 2009/0149929 A1 * | 6/2009 | Levinson et al. ............... 607/99 |
| 2009/0149930 A1 | 6/2009 | Schenck |
| 2009/0312676 A1 * | 12/2009 | Rousso et al. ................. 601/15 |
| 2010/0081971 A1 | 4/2010 | Allison |
| 2010/0280582 A1 | 11/2010 | Baker et al. |
| 2011/0077723 A1 | 3/2011 | Parish et al. |
| 2012/0022518 A1 | 1/2012 | Levinson |
| 2012/0239123 A1 | 9/2012 | Weber |

FOREIGN PATENT DOCUMENTS

| | | |
|---|---|---|
| CN | 1817990 A | 8/2006 |
| DE | 532976 C | 9/1931 |
| DE | 2851602 | 6/1980 |
| DE | 4213584 | 11/1992 |
| DE | 4213584 A1 | 11/1992 |
| DE | 4224595 | 1/1994 |
| EP | 0263069 A2 | 4/1988 |
| EP | 0397043 | 11/1990 |
| EP | 0406244 A1 | 1/1991 |
| EP | 0598824 A1 | 6/1994 |
| GB | 2286660 A | 8/1995 |
| GB | 2323659 A | 9/1998 |
| JP | S6282977 | 4/1987 |
| JP | 63076895 A | 4/1988 |
| JP | 10223961 | 9/1989 |
| JP | 03051964 | 3/1991 |
| JP | 3259975 A | 11/1991 |
| JP | 4093597 A | 3/1992 |
| JP | 7194666 | 8/1995 |
| JP | 7268274 A | 10/1995 |
| JP | 09164163 A | 6/1997 |
| JP | 10216169 | 8/1998 |
| JP | 10216169 A | 8/1998 |
| JP | 3065657 | 11/1999 |
| JP | A2000503154 | 3/2000 |
| JP | A2002543668 | 12/2002 |
| JP | A2004013600 | 1/2004 |
| JP | 2004073812 | 11/2004 |
| JP | A2005039790 | 2/2005 |

(56) References Cited

FOREIGN PATENT DOCUMENTS

| JP | 3655820 | 3/2005 |
|---|---|---|
| JP | 200565984 | 3/2005 |
| JP | 2005110755 | 4/2005 |
| JP | 2005520608 T | 7/2005 |
| JP | 2008323716 | 11/2005 |
| JP | 2006026001 A | 2/2006 |
| JP | A2006520949 | 9/2006 |
| JP | 2008532591 | 8/2008 |
| KR | 1020040094508 | 11/2004 |
| SU | 532976 | 11/1978 |
| TW | 0476644 | 2/2002 |
| WO | WO8503216 | 8/1985 |
| WO | WO94/04116 | 3/1994 |
| WO | WO-9636293 A1 | 11/1996 |
| WO | WO-9637158 A1 | 11/1996 |
| WO | WO97/05828 | 2/1997 |
| WO | WO-9705828 A1 | 2/1997 |
| WO | WO-9722262 A2 | 6/1997 |
| WO | WO9725798 | 7/1997 |
| WO | WO-9841157 A1 | 9/1998 |
| WO | WO-9938469 A1 | 8/1999 |
| WO | WO-0044346 A1 | 8/2000 |
| WO | WO00/65770 | 11/2000 |
| WO | WO0067685 | 11/2000 |
| WO | WO0114012 | 3/2001 |
| WO | WO-0205736 A2 | 1/2002 |
| WO | WO-02102921 A1 | 12/2002 |
| WO | WO03007859 | 9/2003 |
| WO | WO-03078596 A2 | 9/2003 |
| WO | WO03220674 | 11/2003 |
| WO | WO-04000098 A2 | 12/2003 |
| WO | WO-2004080279 A2 | 9/2004 |
| WO | WO2005033957 | 2/2005 |
| WO | WO-2005046540 A1 | 5/2005 |
| WO | WO2006106836 | 5/2006 |
| WO | WO-2006066226 A1 | 6/2006 |
| WO | WO2006094348 | 9/2006 |
| WO | WO-2006127467 A2 | 11/2006 |
| WO | WO2007012083 | 1/2007 |
| WO | WO-2007041642 A2 | 4/2007 |
| WO | WO2008039557 | 4/2008 |
| WO | WO2008143678 | 11/2008 |
| WO | WO2009/011708 | 1/2009 |
| WO | WO2009026471 | 2/2009 |
| WO | WO2010077841 | 7/2010 |
| WO | WO2010127315 | 11/2010 |
| WO | WO2012012296 | 1/2012 |
| WO | WO2012103242 | 8/2012 |

OTHER PUBLICATIONS

U.S. Appl. No. 12/275,002, filed Nov. 20, 2008, Martens.
U.S. Appl. No. 12/275,014, filed Nov. 20, 2008, Martens.
Bohm et al., "Saline-enhanced radiofrequency ablation of breat tissue: an in vitro feasibility study," Invest Radiol, 2000, pp. 149-157, vol. 35—issue (3).
Disclosure re: "Method and Apparatus for Regional Fat Reduction Using Controlled and Sustained Cooling of Skin Surface".
Hale et al., "Influence of chronic heat exposure and prolonged food deprivation on execretion of mahnesium, phosphorus, calcium, hydrogen ion & ketones," Aerosp Med, 1968, pp. 919-926, vol. 39—issue (9).
Heller-Page et al., "Temperature-dependent skin disorders," Journal of the American Academy of Dermatology, May 1988, vol. 18, No. 5, Pt 1, pp. 1003-1019.
Hemmingsson, "Attenuation in Human muscle and Fat Tissue in Vivo and in Vitro," Acta Radiologica Diagnosis 23, 149-151 (1982).
Henry et al.,"Les Dermatoses Hivernales," Rev Med Liege, 1999, 54:11, 864-866. [Abstract Attached].
Holman, "Variation in cryolesion penetration due to probe size and tissue thermal conductivity," Ann. Thorac. Surg. 53, 123-126 (1992).
Hong, "Patterns of Ice Formulation in Normal and Malignant Breast Tissue," Cryobiology 31, 109-120 (1994).

International Search Report and Written Opinion for PCT/US2007/023492; Applicant: Zeltiq Aesthetics, Inc.; Date of Mailing: May 15, 2008, 7 pages.
International Search Report and Written Opinion for PCT/US2007/064016; Applicant: Juniper Medical, Inc.; Date of Mailing: Jul. 20, 2007, 13 pages.
International Search Report and Written Opinion for PCT/US2007/064017; Applicant: Juniper Medical, Inc.; Date of Mailing: Oct. 26, 2007, 16 pages.
International Search Report and Written Opinion for PCT/US2007/064018; Applicant: Juniper Medical, Inc.; Date of Mailing: Jul. 26, 2007, 13 pages.
International Search Report and Written Opinion for PCT/US2007/067638; Applicant: Juniper Medical, Inc.; Date of Mailing: Jan. 10, 2008, 11 pages.
International Search Report and Written Opinion for PCT/US2007/069694; Applicant: Juniper Medical, Inc.; Date of Mailing: Nov. 23, 2007, 12 pages.
International Search Report and Written Opinion for PCT/US2007/075935; Applicant: Zeltiq Aesthetics, Inc.; Date of Mailing: Apr. 10, 2008, 12 pages.
International Search Report and Written Opinion for PCT/US2007/083255; Applicant: Zeltiq Aesthetics, Inc.; Date of Mailing: Aug. 11, 2008, 8 pages.
International Search Report and Written Opinion for PCT/US2008/073930; Applicant: Zeltiq Aesthetics, Inc.; Date of Mailing: Nov. 7, 2008, 10 pages.
International Search Report and Written Opinion for PCT/US2007/062508; Applicant: Juniper Medical, Inc.; Date of Mailing: Jul. 20, 2007, 13 pages.
International Search Report for EP07758558.6; Applicant: Zeltiq Aesthetics, Inc.; Mailed on Jul. 20, 2007, 4 pages.
International Search Report for PCT/US2005/045988; (Apr. 25, 2006).
Kellum, R.E. et al., "Sclerema Neonatorum: Report of Case and Analysis of Subcutaneous and Epidermal-Dermal Lipids by Chromatographic Methods," Arch. Derm., 97:372-80, 1968.
Koska, J. et al., "Endocrine Regulation of Subcutaneous Fat Metabolism During Cold Exposure in Humans," Ann N.Y. Acad, Sci., 967:500-05, 2002.
Kundu et al., "Breath acetone analyzer: diagnostic tool to monitor dietary fat loss," Clin Chem, 1993, pp. 87-92, vol. 39, issue (1).
Kundu et al., "Novel solid-phase assay of ketone bodies in urine," Clin Chem, 1991, pp. 1565-1569, vol. 37—issue (9).
Kuroda et al., "Thermal distribution of radio-frequency inductive hyperthermia using an inductive aperture-type applicator: evaluation of the effect of tumour size and depth," Med Biol Eng Comput, 1999, pp. 285-290, vol. 37—issue (3).
Laugier, et al., "In Vivo Results with a New Device for Ultrasonic Monitoring of Pig Skin Cryosurgery: The Echographic Cryprobe," The society for Investigative Dermatology, Inc., vol. 111(2), Aug. 1998.
Levchenko, et al., "Effect of dehydration on lipid metabolism," WMJ, 1978, pp. 95-97, vol. 50—issue (1).
Lidagoster, MD et al., "Comparison of Autologous Fat Transfer in Fresh, Refridgerated, and Frozen Specimens: An Animal Model Presented," at the 16th Annual Meeting of the Northeastern Society of Plastic Surgeons: Burlington, VT, 1999, pp. 512-515.
Liu, A.Y.C. et al., "Transient Cold Shock Induces the Heat Shock Response upon Recovery at 37 C in Human Cells," J. Biol. Chem., May 20, 1994, 269(20), 14768-14775.
Lvova, "Lipid levels and lipid peroxidation in frog tissues during hypothermia and hibernation," WMJ, 1990, pp. 65-70, vol. 62—issue (1).
Maize, J.C., "Panniculitis," Cutaneous Pathology, Chapter 13:327-344, 1998.
Malcolm, G. et al., "Fatty Acid Composition of Adipose Tissue in Humans: Differences between Subcutaneous Sites," Am J Clin. Nutr., 50(2):288-91, 1989.
Moschella, S.L. et al., "Diseases of the Subcutaneous Tissue," Derm., Section 2:1169-1181, 1985.

(56) References Cited

OTHER PUBLICATIONS

Murphy, J.V. et al., "Frostbite: Pathogensis and Treatment," The Journal of Trauma: Injury, Infection, and Critical Care, 48(1):171-178, 2000.
Nagao et al., "Dietary diacylglycerol suppresses accumulation of body fat compared to triacylglycerol in men a double-blind controlled trial," J Nutr, 2000, pp. 792-797, vol. 130—issue (4).
Nagore et al., "Lipoatrophia semicircularis—a traumatic panniculitis: Report of seven cases and review of the literature," Journal of the American Academy of Dermatology, Nov. 1998, 39:879-81.
Nielsen, "Thermoregulation in Rest and Exercise," Acta Phys Scan Supp, 1969, pp. 6-74, vol. 323.
Nishikawa, "Ultrastructural Changes and Lipid Peroxidation in Rat Adipomusculocutaneous Flap Isotransplants after Normothermic Storage and Reperfusion," Transplantation, 1992, 54, 795-801.
Non-Final Office Action; U.S. Appl. No. 11/435,502; Date of Mailing: Jul. 17, 2009, 10 pages.
Pease, "An Integrated Probe for Magnetic Resonance Imaging Monitored Skin Cryosurgery," Journal of Biomedical Engineering 117, 59-63, (1995).
Pech, "Attenuation values, volume changes and artifacts in tissue due to freezing," Acta Radiologica 6, 779-782 (1987).
Peterson et al., "Bilateral Fat Necrosis of the Scrotum, Urology Service, Department of Surgery, Dermatology Service, Department of Medicine and Department of Pediatrics," Letterman Army Medical Center, Journal of Urology, 1976, pp. 825-826, vol. 116, The Williams & Wilkins Co.
Phinney, S.D. et al., "Human Subcutaneous Adipose Tissue Shows Site-Specific Differences in Fatty Acid Composition," Am J. Clin. Nutr., 60:725-29, 1994.
Rabi, "Metabolic adaptations in brown adipose tissue of the hamster in extreme ambient temperatures," American Journal of Physiology 231, 153-160 (1976).
Renold, A.E., "Adipose Tissue," Handbook of Physiology, Chapter 15:170-76, 1965.
Rubinsky, "Cryosurgery: advances in the application of low temperatures to medicine," Int. J. Refrig. 190-199 (1991).
Schoning, et al., "Experimental Frostbite: Freezing Times, Rewarming Times, and Lowest Temperatures of Pig Skin Exposed to Chilled Air," Cryobiology, 1990, pp. 189-193, 27.
Shephard, "Adaptation to Exercise in the Cold," Sports Medicine, 1985, 2:59-71.
Winkler et al., "Gene Transfer in Laboratory Fish: Model Organisms for the Analysis of Gene Function," Transgenic Animals, 1997, pp. 387-395.
Young, H.E. et al., "Isolation of Embryonic Chick Myosatellite and Pluripotent Stem Cells," J. Tiss. Cult. Meth., 14:85-92, 1992.
Final Office Action; U.S. Appl. No. 10/391,221; Date of Mailing: Aug. 24, 2006, 4 pages.
Final Office Action; U.S. Appl. No. 11/016,196; Date of Mailing: Mar. 23, 2010, 12 pages.
Final Office Action; U.S. Appl. No. 11/435,502; Date of Mailing: Mar. 29, 2010, 11 pages.
International Search Report and Written Opinion for PCT/US2009/058088; Applicant: Zeltiq Aesthetics, Inc.; Date of Mailing: Nov. 20, 2009, 14 pages.
International Search Report and Written Opinion for PCT/US2009/067973; Applicant: Zeltiq Aesthetics, Inc.; Date of Mailing: Feb. 18, 2010, 10 pages.
Non-Final Office Action; U.S. Appl. No. 10/391,221; Date of Mailing: Jan. 25, 2006, 6 pages.
Non-Final Office Action; U.S. Appl. No. 10/391,221; Date of Mailing: May 30, 2007, 8 pages.
Non-Final Office Action; U.S. Appl. No. 10/391,221; Date of Mailing: Jul. 22, 2005, 6 pages.
Non-Final Office Action; U.S. Appl. No. 11/016,196; Date of Mailing: Apr. 22, 2008, 11 pages.
Non-Final Office Action; U.S. Appl. No. 11/016,196; Date of Mailing: Sep. 25, 2009, 8 pages.
Non-Final Office Action; U.S. Appl. No. 11/359,092; Date of Mailing: Nov. 19, 2009, 13 pages.
Non-Final Office Action; U.S. Appl. No. 11/528,225; Date of Mailing: Apr. 12, 2010, 11 pages.
Pre-Interview Office Action; U.S. Appl. No. 11/434,478; Date of Mailing: May 6, 2010, 4 pages.
European Search Report, European Patent Application No. 10167756.5, Applicant: The General Hospital Corporation, Mailing Date: Aug. 31, 2010, 6 pages.
European Search Report, Eurpean Patent Application No. EP07761461; Applicant: Zeltiq Aesthetics, Inc., Mailing Date: Apr. 25, 2012, 9 pages.
European Search Report, Supplement, European Patent Application No. EP08798416.7, Applicant: Zeltiq Aesthetics, Inc., Mailing Date: Jan. 12, 2012, 7 pages.
European Search Report, Supplement, European Patent Application No. EP09836823, Applicant: Zeltiq Aesthetics, Inc., Mailing Date: May 15, 2012, 5 pages.
Final Office Action; U.S. Appl. No. 11/528,225; Date of Mailing: Dec. 29, 2010, 9 pages.
Final Office Action; U.S. Appl. No. 11/558,046; Date of Mailing: Mar. 30, 2011, 17 pages.
Final Office Action; U.S. Appl. No. 11/741,271; Date of Mailing: Jul. 19, 2012, 8 pages.
Final Office Action; U.S. Appl. No. 11/750,953; Date of Mailing: Jul. 5, 2012, 11 pages.
International Search Report and Written Opinion for PCT/US2010/033290; Applicant: Zeltiq Aesthetics, Inc.; Mailed on Feb. 25, 2011, 12 pages.
International Search Report and Written Opinion for PCT/US2011/022112; Applicant: Zeltiq Aesthetics, Inc.; Mailed on Mar. 18, 2011, 11 pages.
International Search Report and Written Opinion for PCT/US2011/022444; Applicant: Zeltiq Aesthetics, Inc., Mailed on Mar. 29, 2011, 14 pages.
International Search Report and Written Opinion for PCT/US2012/022585; Mailed on May 18, 2012, 14 pages.
Merrill, Tom, "A Chill to the Heart: A System to Deliver Local Hypothermia Could One Day Improve the Lives of Heart-Attack Patients," Mechanical Engineering Magazine, Oct. 2010 (10 pages).
Non-Final Office Action; U.S. Appl. No. 11/528,189; Date of Mailing Apr. 6, 2012, 9 pages.
Non-Final Office Action; U.S. Appl. No. 11/528,225; Date of Mailing: Aug. 3, 2011, 11 pages.
Non-Final Office Action; U.S. Appl. No. 11/558,046; Date of Mailing: Jul. 12, 2010, 14 pages.
Non-Final Office Action; U.S. Appl. No. 11/741,271; Date of Mailing: Jul. 12, 2010, 9 pages.
Non-Final Office Action; U.S. Appl. No. 11/777,992; Date of Mailing: Jun. 22, 2012, 5 pages.
Non-Final Office Action; U.S. Appl. No. 12/565,613; Date of Mailing: Sep. 23, 2011, 32 pages.
Non-Final Office Action; U.S. Appl. No. 12/942,852; Date of Mailing: Mar. 7, 2011, 6 pages.
Non-Final Office Action; U.S. Appl. No. 12/942,852; Date of Mailing: Jun. 30, 2011, 10 pages.
Wang et al., "Cryopreservation of cell/hydrogel constructs based on a new cell-assembling technique", Sep. 5, 2009, 40 pages.
Wharton et al., "Cold acclimation and cryoprotectants in a freeze-tolerant Antarctic nematode, *Panagrolaimus davidi*," Mar. 7, 2000, 2 pages.
Manstein et al. "A Novel Cryotherapy Method of Non-invasive, Selective Lipolysis" LasersSurg.Med 40:S20 p. 104 (2008).
Manstein et al."Selective Cryolysis: A Novel Method of Non-Invasive Fat Removal", LasersSurg.Med. 40:595-604 (2008).
Nagle W.A., Soloff, B.L., Moss, A.J. Jr., Henle K.J. "Cultured Chinese Hamster Cells Undergo Apoptosis After Exposure to Cold but Nonfreezing Temperatures" Cryobiology 27, 439-451 (1990).
Mazur, P. "Cryobiology: the Freezing of Biological Systems" Science, 68: 939-949 (1970).
Rubinsky, B., "Principles of Low Temperature Preservation" Heart Failure Reviews, 8, 277-284 (2003).

(56) References Cited

OTHER PUBLICATIONS

Vallerand, A.L., Zamecnik. J., Jones, P.J.H. Jacobs, I. "Cold Stress Increases Lipolysis, FFA RA and TG/FFA Cycling in Humans" Aviation, Space, and Environmental Medicine 70, 42-50 (1999).

Ardevol, "Cooling rates of tissue samples during freezing with liquid nitrogen," J. of Biochem and Biophysical Methods, 27, 77-86 (1993).

Bohm et al., "Saline-enhanced radiofrequency ablation of breat tissue: an in vitro feasibility study," Invest Radio!, 2000, pp. 149-57, vol. 35—issue (3).

Bondei, E. et al., "Disorders of Subcutaneous Tissue (Cold Panniculitis)," Dermatology in General Medicine, Chapter 108, Section 16: 1333-1334, 1993.

Burge, S.M. et al., "Hair Follicle Destruction and Regeneration in Guinea Pig Skin after Cutaneous Freeze Injury," Cryobiology, 27(2): 153-163, 1990.

Coban, "Ischemia-Reperfusion Injury of Adipofascial Tissue: An Experimental Study Evaluating early Histologic and Biochemical Alterations in Rats," Mediators of Inflammation, 2005, 5, 304-308.

Disclosure re: "Method and Apparatus for Regional Fat Reduction Using Controlled and Sustained Cooling of Skin Surface" Date received—2006.

Donski et al., "The Effects of Cooling no Experimental Free Flap Survival," Brit J Plas Surg, 1980, pp. 353-360, vol. 33.

Duncan, W.C. et al., "Cold Panniculitis," Arch. Derm., 94:722-24, 1966.

Epstein, E.H. et al., "Popsicle Panniculitis," The New England Journal of Medicine, 282(17):996-67, 1970.

Gage, "Current Progress in Cryosurgery," Cryobiology 25, 483-486 (1988).

\* cited by examiner

SYSTEMS AND METHODS WITH INTERRUPT/RESUME CAPABILITIES FOR TREATING SUBCUTANEOUS LIPID-RICH CELLS

TECHNICAL FIELD

The present application relates generally to treatment systems and methods with interrupt/resume capabilities for cooling subcutaneous lipid-rich cells.

BACKGROUND

Excess body fat, or adipose tissue, may be present in various locations of the body, including, for example, the thigh, buttocks, abdomen, knees, back, face, arms, chin, and other areas. Moreover, excess adipose tissue is thought to magnify the unattractive appearance of cellulite, which forms when subcutaneous fat protrudes into the dermis and creates dimples where the skin is attached to underlying structural fibrous strands. Cellulite and excessive amounts of adipose tissue are often considered to be unappealing. Moreover, significant health risks may be associated with higher amounts of excess body fat.

A variety of methods have been used to treat individuals having excess body fat and, in many instances, non-invasive removal of excess subcutaneous adipose tissue can eliminate unnecessary recovery time and discomfort associated with invasive procedures such as liposuction. Conventional non-invasive treatments for removing excess body fat typically include topical agents, weight-loss drugs, regular exercise, dieting, or a combination of these treatments. One drawback of these treatments is that they may not be effective or even possible under certain circumstances. For example, when a person is physically injured or ill, regular exercise may not be an option. Similarly, weight-loss drugs or topical agents are not an option when they cause an allergic or negative reaction. Furthermore, fat loss in selective areas of a person's body often cannot be achieved using general or systemic weight-loss methods.

Other methods designed to reduce subcutaneous adipose tissue include laser-assisted liposuction and mesotherapy. Newer non-invasive methods include applying radiant energy to subcutaneous lipid-rich cells via, e.g., radio frequency and/or light energy, such as described in U.S. Patent Publication No. 2006/0036300 and U.S. Pat. No. 5,143,063, or via, e.g., high intensity focused ultrasound (HIFU) radiation such as described in U.S. Pat. Nos. 7,258,674 and 7,347,855. Additional methods and devices for non-invasively reducing subcutaneous adipose tissue by cooling are disclosed in, e.g., Manstein et al. "A Novel Cryotherapy Method of Non-invasive, Selective Lipolysis" Lasers Surg. Med. 40:S20 p 104 (2008), Manstein et al., "Selective Cryolysis: A Novel Method of Non-Invasive Fat Removal", LasersSurg. Med. 40:595-604 (2008), U.S. Pat. No. 7,367,341 entitled "METHODS AND DEVICES FOR SELECTIVE DISRUPTION OF FATTY TISSUE BY CONTROLLED COOLING" to Anderson et al.; U.S. Patent Publication No. 2005/0251120 entitled "METHODS AND DEVICES FOR DETECTION AND CONTROL OF SELECTIVE DISRUPTION OF FATTY TISSUE BY CONTROLLED COOLING" to Anderson et al.; U.S. Patent Publication No. 2007/0198071 entitled "COOLING DEVICE FOR REMOVING HEAT FROM SUBCUTANEOUS LIPID-RICH CELLS" to Ting et al.; U.S. Patent Publication No. 2007/0255362 entitled "CRYOPROTECTANT FOR USE WITH A TREATMENT DEVICE FOR IMPROVED COOLING FOR SUBCUTANEOUS LIPID-RICH CELLS" to Levinson et al.; U.S. Patent Publication No. 2008/0077201 entitled "COOLING DEVICE WITH FLEXIBLE SENSORS" to Levinson et al.; U.S. Patent Publication No. 2008/0077211 entitled "COOLING DEVICE HAVING A PLURALITY OF CONTROLLABLE COOLING ELEMENTS TO PROVIDE A PREDETERMINED COOLING PROFILE" to Levinson et al.; U.S. Patent Publication No. 2008/0287839 entitled "METHOD OF ENHANCED REMOVAL OF HEAT FROM SUBCUTANEOUS LIPID-RICH CELLS AND TREATMENT APPARATUS HAVING AN ACTUATOR" to Rosen et al., filed May 18, 2007; U.S. patent application Ser. No. 11/777,992 entitled "SYSTEM FOR TREATING LIPID-RICH REGIONS" to Levinson et al., filed Jul. 13, 2007, the entire disclosures of which are incorporated herein by reference. Although the methods and devices disclosed in these publications and applications are promising, several improvements for enhancing the implementation of these methods and devices would be desirable.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn are not intended to convey any information regarding the actual shape of the particular elements, and have been solely selected for ease of recognition in the drawings.

DETAILED DESCRIPTION

A. Overview

This document describes apparatus, systems, and methods for cooling subcutaneous adipose tissue. The term "subcutaneous tissue" generally refers to tissue lying beneath the dermis and includes subcutaneous fat, or adipose tissue, which primarily is composed of lipid-rich cells, or adipocytes. Several of the details set forth below are provided to describe the following embodiments and methods in a manner sufficient to enable a person skilled in the relevant art to practice, make, and use them. Several of the details and advantages described below, however, may not be necessary to practice certain embodiments and methods of the invention. Additionally, the invention may include other embodiments and methods that are within the scope of the claims but are not described in detail.

Reference throughout this specification to "one embodiment" or "an embodiment" means that a particular feature, structure, or characteristic described in connection with the embodiment is included in at least one embodiment of the present invention. Thus, the occurrences of the phrases "in one embodiment" or "in an embodiment" in various places throughout this specification are not necessarily all referring to the same embodiment. Furthermore, the particular features, structures, or characteristics may be combined in any suitable manner in one or more embodiments. The headings provided herein are for convenience only and do not limit or interpret the scope or meaning of the claimed invention.

B. Suitable Treatment System

Figure 1:
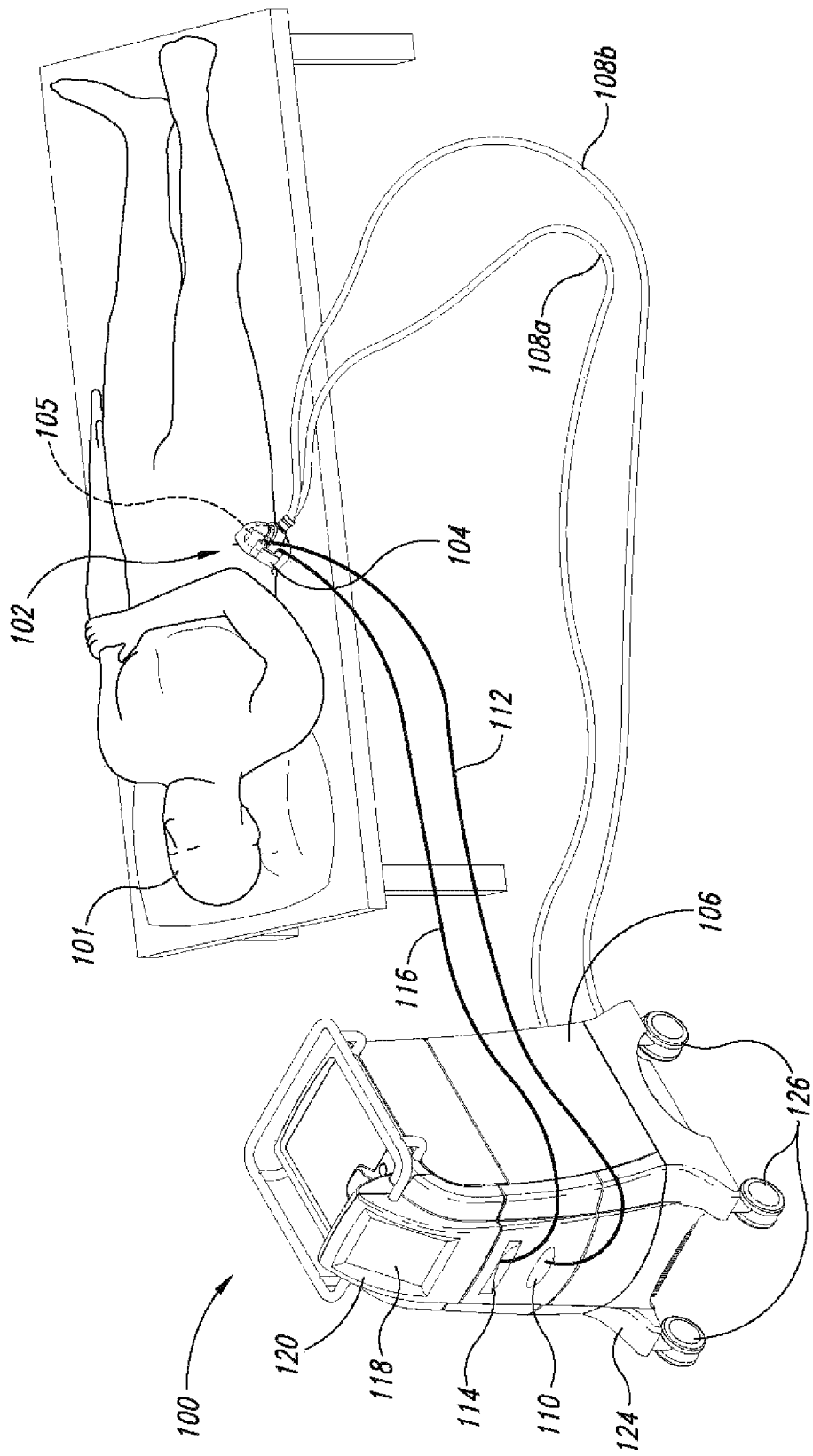
FIG. 1 is an isometric view of a system for treating subcutaneous lipid-rich regions of a subject in accordance with embodiments of the invention.

FIG. 1 and the following discussion provide a brief, general description of a suitable treatment system 100 in which aspects of the disclosure can be implemented. Those skilled in the relevant art will appreciate that the disclosure can be practiced with other treatment systems and treatment protocols, including invasive, minimally invasive, other non-invasive medical treatment systems, and/or combinations of one or more of the above for treating a patient. In general, the term "treatment system", as used generally herein, refers to any of the above system categories of medical treatment as well as any treatment regimes or medical device usage.

The treatment system 100 is suitable for treating a subject's subcutaneous adipose tissue, such as by cooling. The term "subcutaneous tissue" means tissue lying beneath the dermis and includes subcutaneous fat, or adipose tissue, which primarily is composed of lipid-rich cells, or adipocytes. When cooling subcutaneous tissue to a temperature lower than 37° C., subcutaneous lipid-rich cells can selectively be affected, or reduced. In general, the epidermis and dermis of the patient 101 lack lipid-rich cells compared to the underlying lipid-rich cells forming the adipose tissue. Because non-lipid-rich cells usually can withstand colder temperatures better than lipid-rich cells, the subcutaneous lipid-rich cells can selectively be reduced or affected without affecting the non-lipid-rich cells in the dermis, epidermis and other surrounding tissue. In some embodiments, the treatment system 100 can apply cooling temperatures to the skin of the patient in a range of from about −20° C. to about 20° C. In other embodiments, the cooling temperatures can be from about −20° C. to about 10° C., from about 0° C. to about 20° C., from about −15° C. to about 5° C., from about −5° C. to about 15° C., or from about −10° C. to about 0° C.

Without being bound by theory, the selective effect of cooling on lipid-rich cells is believed to result in, for example, membrane disruption, shrinkage, disabling, destroying, removing, killing, or another method of lipid-rich cell alteration. Such alteration is believed to be an intermediate and/or final result of one or more mechanisms acting alone or in combination. It is thought that such mechanism or mechanisms trigger an apoptotic cascade, which is believed to be the dominant form of lipid-rich cell death by non-invasive cooling.

Apoptosis, also referred to as "programmed cell death", is a genetically-induced death mechanism by which cells self-destruct without incurring damage to surrounding tissue. An ordered series of biochemical events induce cells to morphologically change. These changes include cellular blebbing, loss of cell membrane asymmetry and attachment, cell shrinkage, chromatin condensation, and chromosomal DNA fragmentation. Injury via an external stimulus, such as cold exposure, is one mechanism that can induce apoptosis in cells. Nagle, W. A., Soloff, B. L., Moss, A. J. Jr., Henle, K. J. "Cultured Chinese Hamster Cells Undergo Apoptosis After Exposure to Cold but Nonfreezing Temperatures" *Cryobiology* 27, 439-451 (1990).

One aspect of apoptosis, in contrast to cellular necrosis (a traumatic form of cell death causing local inflammation), is that apoptotic cells express and display phagocytic markers on the surface of the cell membrane, thus marking the cells for phagocytosis by, for example, macrophages. As a result, phagocytes can engulf and remove the dying cells (e.g., the lipid-rich cells) without eliciting an immune response. Temperature exposures that elicit these apoptotic events in lipid-rich cells may contribute to long-lasting and/or permanent reduction and reshaping of subcutaneous adipose tissue.

Without being bound by theory, one mechanism of apoptotic lipid-rich cell death by cooling is believed to involve localized crystallization of lipids within the adipocytes at temperatures that do not induce crystallization in non-lipid-rich cells. The crystallized lipids may selectively injure these cells, inducing apoptosis (and may also induce necrotic death if the crystallized lipids damage or rupture the bilayer lipid membrane of the adipocyte). Another mechanism of injury involves the lipid phase transition of those lipids within the cell's bilayer lipid membrane, which results in membrane disruption, thereby inducing apoptosis. This mechanism is well-documented for many cell types and may be active when adipocytes, or lipid-rich cells, are cooled. Mazur, P., "Cryobiology: the Freezing of Biological Systems" Science, 68: 939-949 (1970); Quinn, P. J., "A Lipid Phase Separation Model of Low Temperature Damage to Biological Membranes" Cryobiology, 22: 128-147 (1985); Rubinsky, B., "Principles of Low Temperature Preservation" *Heart Failure Reviews*, 8, 277-284 (2003). Other yet-to-be understood apoptotic mechanisms may exist, based on the relative sensitivity of lipid-rich cells to cooling compared to non-lipid rich cells.

In addition to the apoptotic mechanisms involved in lipid-rich cell death, local cold exposure may induce lipolysis (i.e., fat metabolism) of lipid-rich cells. For example, cold stress has been shown to enhance rates of lipolysis from that observed under normal conditions which serves to further increase the volumetric reduction of subcutaneous lipid-rich cells. Vallerand, A. L., Zamecnik. J., Jones, P. J. H., Jacobs, I. "Cold Stress Increases Lipolysis, FFA Ra and TG/FFA Cycling in Humans" *Aviation, Space and Environmental Medicine* 70, 42-50 (1999).

In various embodiments, the system 100 includes a controller, a computing device, a data acquisition device, a treatment unit, and one or more applicators. The system can employ these components in various embodiments to receive a selection of a treatment profile and apply the selected treatment using an applicator.

FIG. 1 is an isometric view schematically illustrating the treatment system 100 for non-invasively removing heat from subcutaneous lipid-rich regions of a subject patient 101 in accordance with an embodiment of the disclosure. The system 100 can include a treatment device 104 including an applicator 105 that engages a target region of the subject 101. The treatment device 104 can be placed, for example, at an abdominal area 102 of the subject 101 or another suitable area for cooling or removing heat from the subcutaneous lipid-rich cells of the subject 101. It will be understood that treatment devices 104 and applicators 105 can be provided having various, configurations, shapes and sizes suitable for different body regions and body parts such that any suitable area for removing heat from a subcutaneous lipid-rich region of the subject 101 can be achieved.

An applicator, such as applicator 105, is a component of the system 100 that cools a region of a subject 101, such as a human or animal (i.e., "patient"). Various types of applicators may be applied during treatment, such as a vacuum applicator, a belt applicator (either of which may be used in combination with a massage or vibrating capability), and so forth. Each applicator may be designed to treat identified portions of the patient's body, such as chin, cheeks, arms, pectoral areas, thighs, calves, buttocks, abdomen, "love handles", back, and so forth. For example, the vacuum applicator may be applied at the back region, and the belt applicator can be applied around the thigh region, either with or without massage or vibration. Exemplary applicators are described in, e.g., commonly assigned U.S. Patent Publication Nos. 2007/0198071, 2008/0077201, 2008/0077211, and 2008/0287839.

In further embodiments, the system 100 may also include a patient protection device (not shown) incorporated into or configured for use with the applicator that prevents the applicator from directly contacting a patient's skin and thereby reducing the likelihood of cross-contamination between patients, minimizing cleaning requirements for the applicator. The patient protection device may also include or incorporate various storage, computing, and communications devices, such as a radio frequency identification (RFID) component, allowing for example, monitoring and/or metering usage as described in U.S. patent application Ser. No. 11/777,992; U.S. patent application Ser. No. 11/777,995, entitled "LIMITING USE OF DISPOSABLE SYSTEM PATIENT PROTECTION DEVICES" to Levinson et al., filed Jul. 13, 2007; U.S. patent application Ser. No. 11/777,999, entitled "MANAGING SYSTEM TEMPERATURE TO REMOVE HEAT FROM LIPID-RICH REGIONS" to Levinson et al., filed Jul. 13, 2007; U.S. patent application Ser. No. 11/778,001, entitled "USER INTERFACES FOR A SYSTEM THAT REMOVES HEAT FROM LIPID-RICH REGIONS" to Levinson et al., filed Jul. 13, 2007; and U.S. patent application Ser. No. 11/778,003, entitled "SECURE SYSTEMS FOR REMOVING HEAT FROM LIPID-RICH REGIONS" to Levinson et al., filed Jul. 13, 2007, the entire disclosures of which are incorporated herein by reference. Exemplary patient protection devices are described in commonly assigned U.S. Patent Publication No. 2008/0077201.

In the present example, the system 100 can further include a treatment unit 106 and supply and return fluid lines 108a-b between the treatment device 104 and the treatment unit 106. A treatment unit 106 is a device that, based on variable power input, can increase or decrease the temperature at a connected treatment device 104 that in turn may be attached to or incorporated into the applicator 105. The treatment unit 106 can remove heat from a circulating coolant to a heat sink and provide a chilled coolant to the treatment device 104 via the fluid lines 108a-b. Alternatively, treatment unit 106 can circulate warm coolant to the treatment device 104 during periods of warming. Examples of the circulating coolant include water, glycol, synthetic heat transfer fluid, oil, a refrigerant, and/or any other suitable heat conducting fluid. The fluid lines 108a-b can be hoses or other conduits constructed from polyethylene, polyvinyl chloride, polyurethane, and/or other materials that can accommodate the particular circulating coolant. The treatment unit 106 can be a refrigeration unit, a cooling tower, a thermoelectric chiller, or any other device capable of removing heat from a coolant. Alternatively, a municipal water supply (e.g., tap water) can be used in place of the treatment unit 106. One skilled in the art will recognize that there are a number of other cooling technologies that could be used such that the treatment unit or chiller need not be limited to those described herein.

In this example, the treatment device 104 includes at least one applicator 105 and at least one treatment unit 106. The applicator 105 can provide mechanical energy to create a vibratory, massage, and/or pulsatile effect. The applicator 105 can include one or more actuators, such as, motors with eccentric weight, or other vibratory motors such as hydraulic motors, electric motors, pneumatic motors, solenoids, other mechanical motors, piezoelectric shakers, and so on, to provide vibratory energy to the treatment site. Further examples include a plurality of actuators for use in connection with a single treatment device 104 and/or applicator 105 in any desired combination. For example, an eccentric weight actuator can be associated with one treatment device 104 or applicator 105, while a pneumatic motor can be associated with another section of the same treatment device or applicator. This, for example, would give the operator of the treatment system 100 options for differential treatment of lipid rich cells within a single region or among multiple regions of the subject 101. The use of one or more actuators and actuator types in various combinations and configurations with a treatment device 104 or applicator 105 may be possible.

The treatment device 104 can include one or more heat exchanging units. The heat exchanging unit can be a Peltier-type thermoelectric element, and the treatment device 104 can have multiple individually controlled heat exchanging units (e.g., between 1 and 50, between 10 and 45; between 15 and 21, approximately 100, etc.) to create a custom spatial cooling profile and/or a time-varying cooling profile. Each custom treatment profile can include one or more segments, and each segment can include a specified duration, a target heat flux or temperature, and control parameters for features such as vibration, massage, vacuum, and other treatment modes. Treatment devices having multiple individually controlled heat exchanging units are described in commonly assigned U.S. Patent Publication No. 2008/0077211. Embodiments of a treatment device 104 usable with the treatment system 100 are described in more detail below with reference to FIG. 2.

The system 100 can further include a power supply 110 and a controller 114 operatively coupled to the treatment device 104 and the applicator 105. In one embodiment, the power supply 110 can provide a direct current voltage to the thermoelectric treatment device 104 and/or the applicator 105 to remove heat from the subject 101. The controller 114 can monitor process parameters via sensors (not shown) placed proximate to the treatment device 104 via a control line 116 to, among other things, adjust the heat removal rate based on the process parameters. The controller 114 can further monitor process parameters to adjust the applicator 105 based on treatment parameters, such as treatment parameters defined in a custom treatment profile or patient-specific treatment plan.

The controller 114 can exchange data with the applicator 105 via an electrical line 112 or, alternatively, via a wireless or an optical communication link. Note that control line 116 and electrical line 112 are shown in FIG. 1 without any support structure. Alternatively, control line 116 and electrical line 112 (and other lines including, but not limited to fluid lines 108a-b) may be bundled into or otherwise accompanied by a conduit or the like to protect such lines, enhance ergonomic comfort, minimize unwanted motion (and thus potential inefficient removal of heat from subject 101), and to provide an aesthetic appearance to system 100. Examples of such a conduit include a flexible polymeric, fabric, or composite sheath, an adjustable arm, etc. Such a conduit (not shown) may be designed (via adjustable joints, etc.) to "set" the conduit in place for the treatment of subject 101.

The controller 114 can include any processor, Programmable Logic Controller, Distributed Control System, secure processor, and the like. A secure processor can be implemented as an integrated circuit with access-controlled physical interfaces; tamper resistant containment; means of detecting and responding to physical tampering; secure storage; and shielded execution of computer-executable instructions. Some secure processors also provide cryptographic accelerator circuitry. Secure storage may also be implemented as a secure flash memory, secure serial EEPROM, secure field programmable gate array, or secure application-specific integrated circuit.

In another aspect, the controller 114 can receive data from an input device 118 (shown as a touch screen), transmit data to an output device 120, and/or exchange data with a control panel (not shown). The input device 118 can include a keyboard, a mouse, a stylus, a touch screen, a push button, a switch, a potentiometer, a scanner, or any other device suitable for accepting user input. The output device 120 can include a display or touch screen, a printer, a medium reader, an audio device, any combination thereof, and any other device or devices suitable for providing user feedback. In the embodiment of FIG. 1, the output device 120 is a touch screen that functions as both an input device 118 and an output device 120. The control panel can include visual indicator devices or controls (e.g., indicator lights, numerical displays, etc.) and/or audio indicator devices or controls. The control panel may be a component separate from the input device 118 and/or output device 120, may be integrated with one or more of the devices, may be partially integrated with one or more of the devices, may be in another location, and so on. In alternative examples, the control panel, input device 118, output device 120, or parts thereof (described herein) may be contained in, attached to, or integrated with the treatment device 104 and/or applicator 105. In this example, the controller 114, power supply 110, control panel, treatment unit 106, input device 118, and output device 120 are carried by a rack 124 with wheels 126 for portability. In alternative embodiments, the controller 114 can be contained in, attached to, or integrated with the treatment device 104 and/or the applicator 105 and/or the patient protection device described above. In yet other embodiments, the various components can be fixedly installed at a treatment site. Further details with respect to components and/or operation of treatment device 104, treatment unit 106, applicator 105 and other components may be found, for example, in commonly-assigned U.S. Patent Application Publication Nos. 2008/0287839 and 2008/0077201.

In operation, and upon receiving input to start a treatment protocol, the controller 114 can cause the applicator 105 to cycle through each segment of a prescribed treatment plan. In so doing, the applicator 105 applies power to one or more treatment devices 104, such as thermoelectric coolers (e.g., TEC "zones"), to begin a cooling or heating cycle and, for example, activate features or modes such as vibration, massage, vacuum, etc. Using sensors (not shown) proximate to the one or more treatment devices 104, the patient's skin, a patient protection device, or other locations or combinations thereof, the controller 114 determines whether a temperature or heat flux that is sufficiently close to the target temperature or heat flux has been reached. It will be appreciated that while a region of the body (e.g., adipose tissue) has been cooled or heated to the target temperature or by a target heat flux, in actuality that region of the body may be close but not equal to the target temperature, e.g., because of the body's natural heating and cooling variations. Thus, although the system may attempt to heat or cool to the target temperature or by a target heat flux, a sensor may measure a sufficiently close temperature. If the target temperature has not been reached, power can be increased or decreased to change heat flux, as needed, to maintain the target temperature. When the prescribed segment duration expires, the controller 114 may apply the treatment parameters (e.g., heat flux or duration) indicated in the next treatment profile segment. In some embodiments, heat flux or temperature can be controlled using a variable other than, or in addition to, power.

During treatment, the treatment process may be interrupted. As used herein, the word "interrupted" generally refers to being in a state in which the treatment process may not safely and/or effectively proceed. For example, the treatment process may be interrupted when the applicator 105 is detached from the patient. In another example, the treatment process may be interrupted when the sensors (not shown) indicate freezing of the adipose tissue or when the treatment quality is unsatisfactory. In a further example, an operator or the patient may pause the treatment process using, e.g., the input device 118. In yet further examples, the treatment process may be interrupted based on other suitable conditions.

The interrupted treatment may cause operational difficulties and/or safety concerns for the patient. For example, if the operator restarts the treatment process from the initial stages of the treatment plan, the additional cooling or heating may be excessive to injure the adipose tissue of the patient. If the operator simply continues the treatment process, the adipose tissue of the patient may be insufficiently cooled or heated because of blood circulation and/or other physiological activities of the patient during the period of treatment interruption. As a result, the treatment process may not achieve the desired effect. Several embodiments of the treatment system 100 can at least reduce the impact of such interruptions by monitoring for an interruption and performing a recovery process to compensate for the interruption, as described in more detail below with reference to FIGS. 4-8.

Although a noninvasive applicator is illustrated and discussed herein, minimally invasive applicators may also be employed in connection with a noninvasive applicator. In such a case, the applicator and patient protection device may be integrated. As an example, a cryoprobe that may be inserted directly into the subcutaneous adipose tissue to cool or freeze the tissue is an example of such a minimally invasive applicator. Cryoprobes manufactured by, e.g., Endocare, Inc., of Irvine, Calif. are suitable for such applications. This patent application incorporates by reference U.S. Pat. No. 6,494,844, entitled "DEVICE FOR BIOPSY AND TREATMENT OF BREAST TUMORS"; U.S. Pat. No. 6,551,255, entitled "DEVICE FOR BIOPSY OF TUMORS"; U.S. Patent Publication No. 2007/0055173, entitled "ROTATIONAL CORE BIOPSY DEVICE WITH LIQUID CRYOGEN ADHESION PROBE"; U.S. Pat. No. 6,789,545, entitled "METHOD AND SYSTEM FOR CRYOABLATING FIBROADENOMAS"; U.S. Patent Publication No. 2004/0215294, entitled "CRYOTHERAPY PROBE"; U.S. Pat. No. 7,083,612, entitled "CRYOTHERAPY SYSTEM"; U.S. Patent Publication No. 2005/0261753, entitled "METHODS AND SYSTEMS FOR CRYOGENIC COOLING", and U.S. patent application Ser. No. 11/933,066, entitled "METHOD AND APPARATUS FOR COOLING SUBCUTANEOUS LIPID-RICH CELLS OR TISSUE" to Ebbers et al., filed Oct. 31, 2007.

Figure 2:
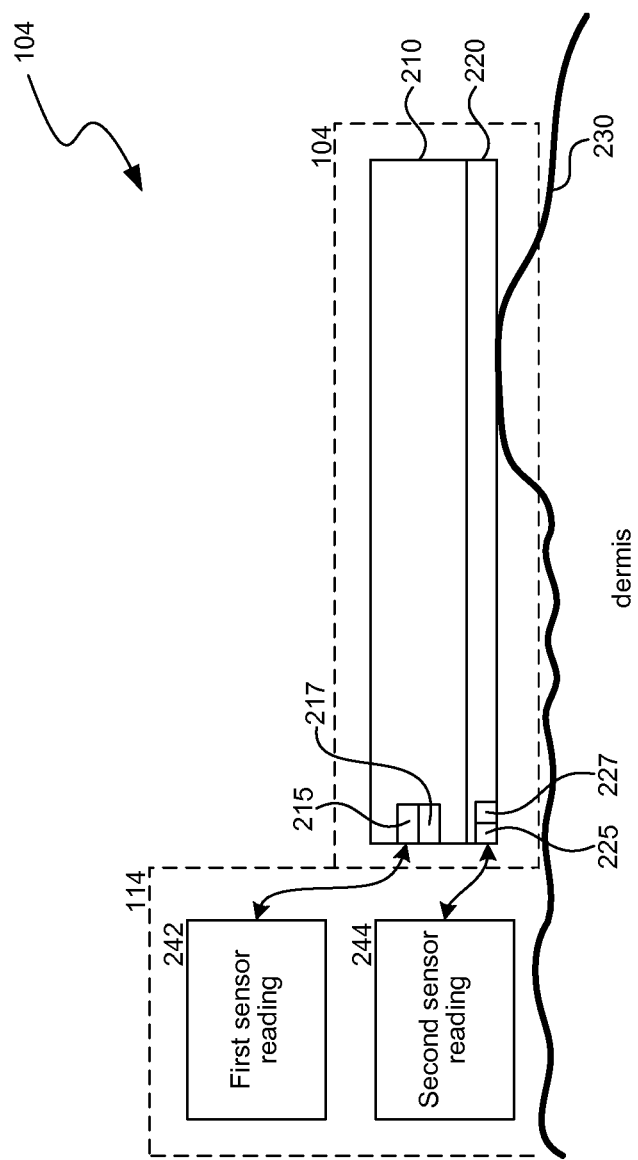
FIG. 2 is a partial cross-sectional view illustrating a treatment device suitable to be used in the system of FIG. 1 in accordance with embodiments of the invention.

FIG. 2 is a schematic diagram illustrating the treatment device 104 for removing heat from subcutaneous lipid-rich cells in accordance with one embodiment. The treatment device 104 may include a heat exchanging unit, such as a heat exchanging plate 210, and an interface layer 220. The interface layer 220 may be a plate, a film, a covering, or other suitable materials described herein and may serve as the patient protection device described herein. The interface layer 220 is located between the heat exchanging plate 210 and the skin 230 of a subject (not shown), such as the skin of a patient receiving treatment via the treatment device 104. The heat exchanging plate 210 may contain a communication component 215 that communicates with the controller 114 to provide a first sensor reading 242 as described herein, and a sensor 217 that measures, e.g., the temperature of the heat exchanging plate 210 or heat flux across a surface of or plane within the heat exchanging plate 210. The interface layer 220 may also contain a similar communication component 225 that communicates with the controller 114 to provide a second sensor reading 244 and a sensor 227 that measures, e.g., the temperature of the interface layer 220 or heat flux across a surface of or plane within the interface layer 220. For example, one or both of communication components 215, 225 may receive and transmit information from the controller 114, such as temperature and/or heat flux information as determined by one or both of the sensors 217, 227. The treatment device 104 may also contain power components and other components described with respect to FIG. 1 and related applications.

In certain embodiments, the interface layer 220 of the treatment device 104 may include a sleeve for contacting the patient's skin 230. The sleeve may include a first sleeve portion (not shown) and a second sleeve portion (not shown) extending from the first sleeve portion. The first sleeve portion may contact and/or facilitate the contact of the treatment device 104 with the patient's skin 230. The second sleeve portion may be an isolation layer extending from the first sleeve portion. The second sleeve portion may be constructed from latex, rubber, nylon, Kevlar®, or other substantially impermeable or semi-permeable material. The second sleeve portion may prevent contact between the patient's skin 230 and the heat exchanging plates, among other things. Further details regarding a suitable sleeve may be found in U.S. Patent Publication No. 2008/0077201.

In other embodiments, the treatment device 104 may include a belt that assists in forming a contact between the treatment device 104 (such as via an interface layer 220) and the patient's skin 230. For example, the treatment device 104 may include retention devices (not shown) coupled to a frame. The retention devices may be rotatably connected to the frame by a plurality of coupling elements that may be, for example, pins, ball joints, bearings, or other type of rotatable joints. Alternatively, the retention devices may be rigidly affixed to the end portions of heat exchanging element housings. Further details regarding a suitable belt device may be found in U.S. Patent Publication No. 2008/0077211.

In further embodiments, the treatment device 104 may include a vacuum (not shown) that assists in forming a contact between the treatment device 104 (such as via the interface layer 220) and the patient's skin 230. For example, the treatment device 104 may provide mechanical energy to a treatment region. Imparting mechanical vibratory energy to the patient's tissue by repeatedly applying and releasing a vacuum to the subject's tissue, for instance, creates a massage action during treatment. Further details regarding a vacuum type device may be found in U.S. Patent Application Publication No. 2008/0287839.

C. Computing System Software Modules

Figure 3:
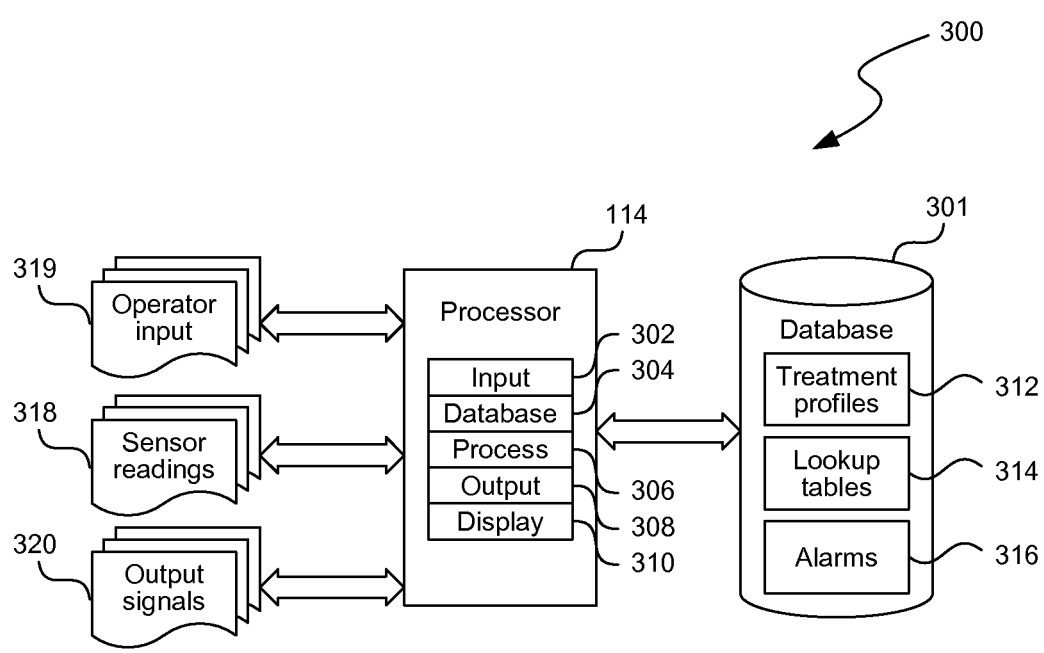
FIG. 3 is a block diagram showing computing system software modules for removing heat from subcutaneous lipid-rich cells in accordance with embodiments of the invention.

FIG. 3 is a functional diagram showing software modules 300 suitable for use in the controller 114 of FIG. 1. Each component may be a computer program, procedure, or process written as source code in a conventional programming language, such as C, C+, C++, C# etc., and may be presented for execution by a CPU of the controller 114. The various implementations of the source code and object byte codes may be stored on a computer-readable storage medium. The modules of controller 114 may include an input module 302, a database module 304, a process module 306, an output module 308, and, optionally, a display module 310 interconnected with one another.

In operation, the input module 302 accepts an operator input 319, such as process setpoint (e.g., a target heat flux or temperature) and control selections (e.g., a resume/terminate selection), and communicates the accepted information or selections to other components for further processing. The database module 304 organizes records, including treatment profiles 312, lookup tables 314, and alarms 316, and facilitates storing and retrieving of these records to and from a database 301. The treatment profiles 312 may include various therapies for treating different areas of the subject 101 (FIG. 1). For example, the treatment profiles 312 may include a pre-cooling duration, a steady state duration, a termination duration, and/or other suitable parameters for a treatment process. The lookup tables 314 may include values of temperatures of adipose tissue and corresponding time of cooling or warming. Any type of database organization may be utilized, including a flat file system, hierarchical database, relational database, or distributed database, such as provided by a database vendor such as Oracle Corporation, Redwood Shores, Calif.

The process module 306 generates control variables based on sensor readings 318 from sensors (e.g., the temperature measurement components 217 and 227 of FIG. 2) and/or other data sources, and the output module 308 generates output signals 320 based on the control variables. The controller 114 optionally may include the display module 310 for displaying, printing, or downloading the sensor readings 318, output signals 320, and/or other information via devices such as the output device 120 (FIG. 1). A suitable display module 310 may include a video driver that enables the controller 114 to display the sensor readings 318 or other status of treatment resumption on the output device 120.

Figure 4:
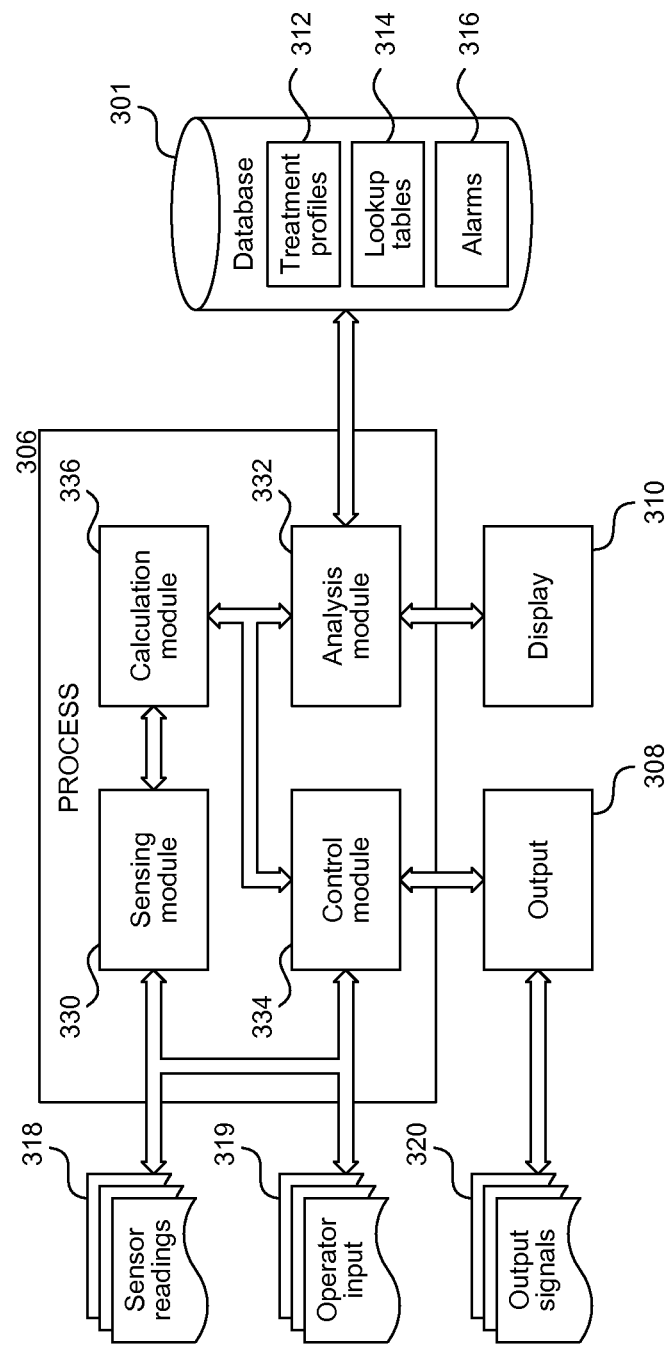
FIG. 4 is a block diagram showing a process module suitable to be used in the computing system of FIG. 3.

FIG. 4 is a block diagram showing an embodiment of the process module 306 of FIG. 3. The process module 306 may further include a sensing module 330, an analysis module 332, a control module 334, and a calculation module 336 interconnected with one other. Each module may be a computer program, procedure, or routine written as source code in a conventional programming language, or one or more modules may be hardware modules.

The sensing module 330 is configured to receive and convert the sensor readings 318 into parameters in desired units. For example, the sensing module 330 may receive the sensor readings 318 as electrical signals (e.g., a voltage or a current) and convert the electrical signals into instant temperatures in Celsius. In another example, the sensing module 330 may convert the electrical signals into an oxygen depletion level in the treated area as an indicator of hypoxia or ischemia. The sensing module 330 may have routines including, for example, linear interpolation, logarithmic interpolation, data mapping, or other routines to associate the sensor readings 318 to parameters in desired units.

The calculation module 336 may include routines configured to perform various types of calculation to facilitate operation of other modules. For example, the calculation module 336 may include counters, timers, and/or other suitable accumulation routines for deriving an elapsed time of treatment (t), an elapsed time since an interruption ($\tau$), and/or other parameters associated with the interruption. Further, the calculation module 336 may include routines configured to calculate tissue temperatures at different times during treatment based on temperature parameters, heat flux parameters, and/or other suitable parameters.

In certain embodiments, the calculation module 336 may also include a computation routine for deriving an interruption temperature ($T_{interrupt}$) of the adipose tissue based on the measured temperatures from at least one of the sensors 217 and 227 according to the following formula:

$$T_{interrupt} = T_o e^{-kt} \quad \text{(Equation I)}$$

where $T_o$ is an initial temperature of the adipose tissue (e.g., 37° C.) and k is a time constant associated with cooling the adipose tissue. The cooling time constant k may be empirically derived for a particular interface temperature (e.g., 0° C.) between the cooling plate 210 (FIG. 2) and the skin 230 of the subject 101 (FIG. 2) by performing an exponential curve fitting on a tissue temperature versus time plot (e.g., the plot shown in FIG. 7) and/or other suitable techniques. Equation I may also be used to derive an instant temperature of the adipose tissue during cooling.

In other embodiments, the calculation module 336 may also include another computation routine for deriving a rewarming temperature ($T_{rewarm}$) of the adipose tissue after the interruption according to the following formula:

$$T_{rewarm} = T_{interrupt} e^{-m\tau} \quad \text{(Equation II)}$$

where m is a time constant associated with rewarming the adipose tissue. The rewarming time constant m may also be empirically derived for a particular ambient temperature (e.g., 25° C.) by performing an exponential curve fitting on a tissue temperature versus time plot (e.g., the plot shown in FIG. 8) and/or other suitable techniques.

Figure 7:
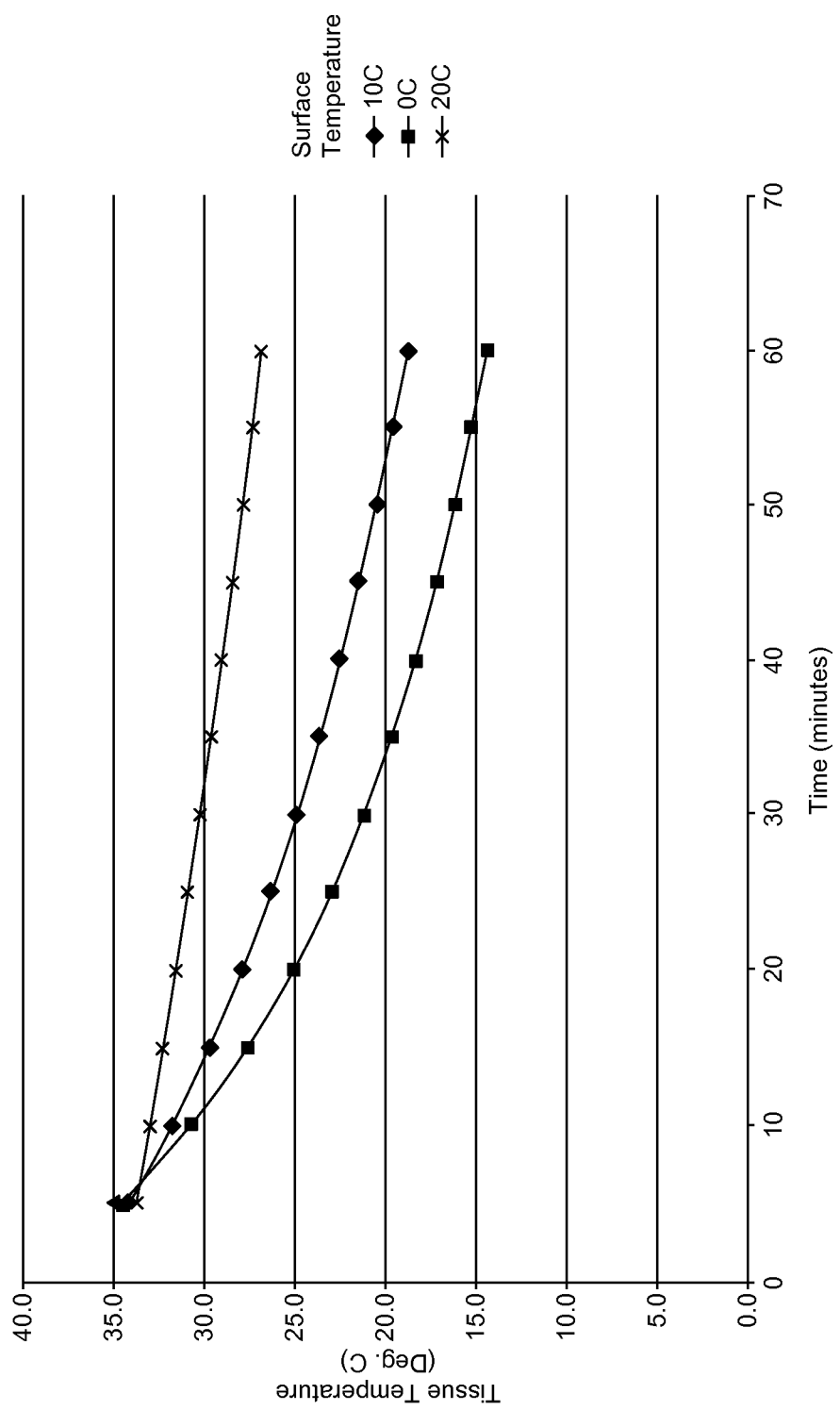
FIG. 7 is an example of a tissue temperature versus time plot during cooling adipose tissue.
Figure 8:
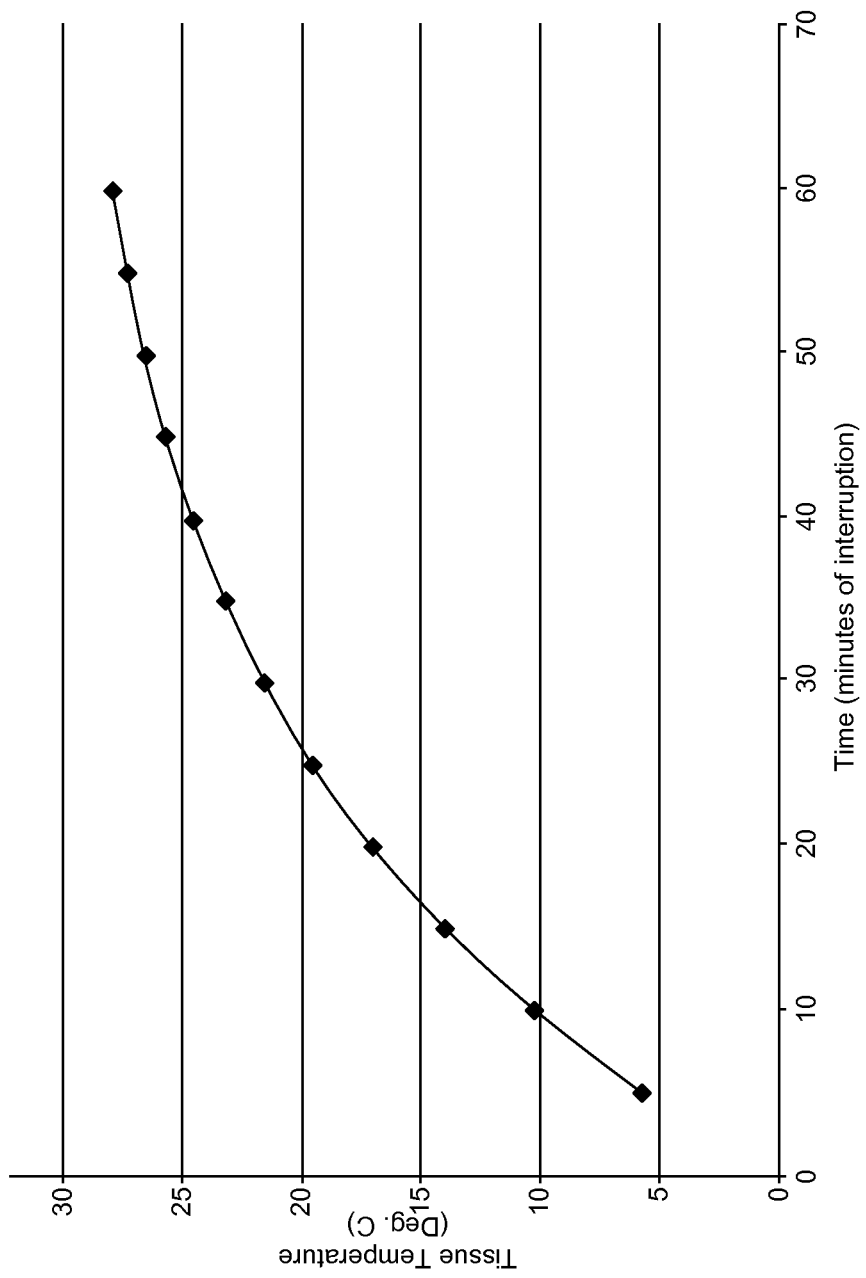
FIG. 8 is an example of a tissue temperature versus time plot during rewarming adipose tissue.

In further embodiments, the calculation module 336 may include a lookup routine to derive the interruption temperature ($T_{interrupt}$) and/or the rewarming temperature ($T_{rewarm}$) of the adipose tissue based on the lookup tables 314 stored in the database 301 or plots of temperature versus time for cooling and/or rewarming of the adipose tissue. Examples of such temperature versus time plots for cooling and rewarming are shown in FIGS. 7 and 8, respectively.

In yet further embodiments, thermal modeling of different tissue and/or applicator geometries may result in different equations for deriving the interruption temperature of Equation I ($T_{interrupt}$) and/or the rewarming temperature of Equation II ($T_{rewarm}$). Moreover, even though the foregoing description is directed toward a process for cooling the adipose tissue, in other embodiments, the calculation module 336 may also include other suitable computation routines for calculating the interruption temperature and/or other parameters of the adipose tissue during a process for heating, or a combination of heating and cooling the adipose tissue.

In yet further embodiments, the calculation module 336 may also be configured to derive a rate of change for the interface temperature according to the following formula:

$$\frac{dT}{dt} \approx \frac{T_{i+1} - T_i}{\Delta t} \quad \text{(Equation III)}$$

where $T_{i+1}$ is the temperature record number i+1, $T_i$ is the previous temperature record, and $\Delta t$ is the time difference between the two temperature records. The calculation module 336 may be configured to derive a rate of change of the temperature of the adipose tissue in a similar fashion.

The calculation module 336 may also be configured to derive a profile for a recovery process in response to the interruption. For example, the calculation module 336 may include a computation routine for calculating an amount of heat (Q) that must be removed from the adipose tissue to return the adipose tissue to the temperature at the time of the interruption as follows:

$$Q = \rho V C_p (T_{rewarm} - T_{interrupt}) \quad \text{(Equation IV)}$$

where $\rho$ is the density of the adipose tissue (e.g., about 918 kg/m$^3$); V is a volume of the adipose tissue that approximately corresponds to a cross-sectional area of the cooling plate 210 and a thickness of the adipose tissue (e.g., about 0.1 m to about 0.2 m); and $C_p$ is the specific heat capacity of the adipose tissue (e.g., about 3.5 kJ/kg° C.).

The density and specific heat capacity of the adipose tissue may empirically be determined. In certain embodiments, the operator may adjust the thickness of the adipose tissue, select a value from a list of available options, or enter a value determined by direct measurement involving, for example, ultrasound, calipers, electrical conductance, etc. In other embodiments, the thickness of the adipose tissue may automatically be set based on a particular treatment area (e.g., thighs, buttocks, etc.)

The calculation module 336 may also include another computation routine for deriving a desired cooling rate ($\dot{Q}$) for the recovery process as follows:

$$\dot{Q} = \frac{Q}{\pi} = \frac{\rho V C_p (T_{rewarm} - T_{interrupt})}{\pi} \quad \text{(Equation V)}$$

where $\pi$ is a recovery duration. In certain embodiments, the operator may set the recovery duration ($\pi$) to any desired value with or without bounds. In other embodiments, the recovery duration ($\pi$) may be preselected and inaccessible to the operator.

In certain embodiments, the calculation module 336 may further include a computation routine for calculating an expected average rate of change in the temperature of the adipose tissue during the recovery period as follows:

$$\Delta T = \frac{(T_{rewarm} - T_{interrupt})}{\pi} \quad \text{(Equation VI)}$$

In other embodiments, the expected rate of change may also be based on the interface temperature between the cooling plate 210 and the skin 230 of the subject 101.

The analysis module 332 may be configured to analyze parameters from the sensing module 330 and the calculation module 336 and to determine (1) whether an interruption has occurred; and (2) whether the treatment process may be resumed. The display module 310 may then receive the determined results for output to the operator. In certain embodiments, the analysis module 332 may indicate an interruption when the following conditions occur:

The input module 302 (FIG. 3) receives an interruption indication from the operator and/or the subject 101.

The calculated rate of change for the measured skin temperature is above (or below) a threshold (e.g., 0.1° C./sec), or alternatively, the measured heat flux across the skin is above (or below) a threshold (e.g., 50 mW/cm$^2$).

The measured bio-resistance of the skin 230 of the subject 101 is above a threshold.

In other embodiments, the analysis module 332 may indicate an interruption based on other suitable conditions. In further embodiments, the analysis module 332 can also generate an alarm after an interruption is indicated and store the alarm in the database 301 as alarms 316.

The analysis module 332 may also be configured to determine whether the treatment process may be resumed based on the following conditions:

If the elapsed time since the interruption (τ) is not less than a difference between the elapsed time of treatment (t) and a preselected ramp time (A) as follows:

$$\tau \geq (t-A),$$

the analysis module 332 indicates that the process cannot be resumed. In one embodiment, the preselected ramp time (A) may be the time required to cool the interface layer 220 to a desired treatment temperature. In other embodiments, the preselected ramp time (A) may have other desired values; or If the elapsed time since the interruption (τ) is greater than a preselected maximum interruption time (B) as follows:

$$\tau \geq B;$$

the analysis module 332 indicates that the process cannot be resumed. In one embodiment, the maximum interruption time (B) may have a value at which the adipose tissue would have been sufficiently rewarmed (e.g., 10 minutes). In other embodiments, the maximum interruption time (B) may have other desired values; or If the treatment process has been interrupted for more than a preselected number of occurrences (e.g., 2 times), the analysis module 332 indicates that the process cannot be resumed.

In other embodiments, the analysis module 332 may indicate that the process cannot be resumed based on other suitable conditions.

The control module 334 may be configured to determine whether the recovery process should be initiated. In one embodiment, if the analysis module 332 indicates that an interruption has occurred and the treatment process may be resumed, the control module 334 may automatically initiate the recovery process. In another embodiment, the display module 310 may output the result from the analysis module 332 and prompt the operator for input. The input module 302 (FIG. 3) may accept and then transmit the operator input 319 to the control module 334 for determining whether to initiate the recovery process or terminate the treatment process. In further embodiments, the control module 334 can determine whether to initiate the recovery process based on other suitable conditions.

The control module 334 may also be configured to monitor parameters of the recovery process and adjust the recovery process based on the monitored parameters. In one embodiment, the control module 334 may monitor a rate of change of the temperature of the adipose tissue and/or the interface temperature during the recovery process. If the monitored rate of change is below the expected rate of change from Equation VI by a preselected amount (e.g., 25%), then the control module 334 may (1) increase a power output to the cooling plate 210 by a preselected amount or by a proportional-derivative-integral (PID) routine using the rate of change as a process variable; and/or (2) increase the recovery duration by a preselected amount (e.g., 3 minutes); otherwise, the control module 334 continues to monitor the recovery process. In other embodiments, the control module 334 may also monitor a heat flux, a thermal image, and/or other parameters of the recovery process.

D. Treatment Resumption Methods

Figure 5:
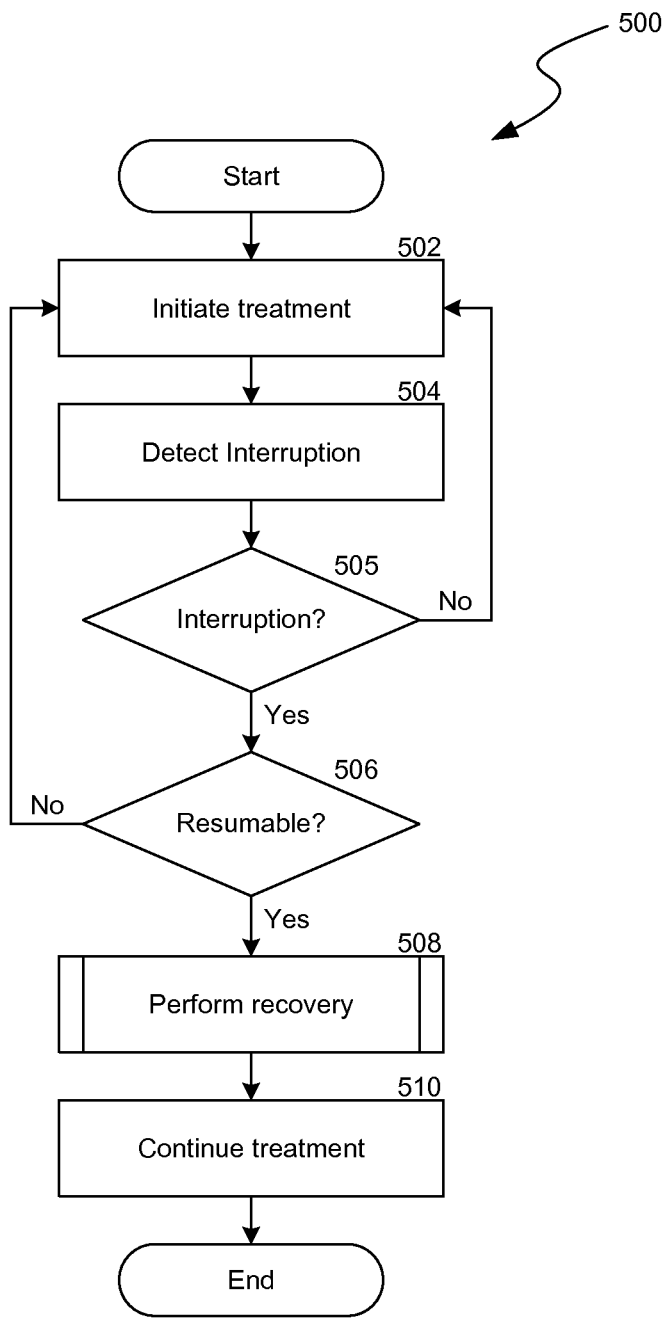
FIG. 5 is a flow diagram showing a method for treating subcutaneous lipid-rich regions of a subject in accordance with embodiments of the invention.

FIG. 5 is a flow diagram illustrating a method 500 for treating subcutaneous lipid-rich regions of a subject in accordance with embodiments of the invention. Even though the method 500 is described below with reference to the treatment system 100 of FIG. 1, the treatment device 104 of FIG. 2, and the software modules of FIGS. 3 and 4, the method 500 may also be applied in other treatment systems with additional or different hardware and/or software components.

As shown in FIG. 5, an early stage 502 of the method 500 may include initiating a treatment process for the subject. In one embodiment, initiating the treatment process may include receiving an initiation input with the input module 302 via, for example, the input device 118 and retrieving a suitable treatment profile from the database 301. Then the control module 334 may activate the treatment device 104 and/or other components of the treatment system 100 to remove heat from the skin 230 of the subject 101 (FIG. 2) according to the retrieved treatment profile. The calculation module 336 may accumulate the elapsed time of treatment by, for example, activating an internal timer or counter.

Another stage 504 of the method 500 may include detecting an interruption in the treatment process. In one embodiment, detecting the interruption may include accepting an input for pause from the operator and/or the subject 101 by the input module 302. In other embodiments, detecting an interruption may include continuously sensing an interface temperature between the cooling plate 210 and the skin 230 of the subject 101 with the sensing module 330, calculating a rate of change for the sensed temperature with the calculation module 336, and analyzing the calculated rate of change of the sensed temperature with the analysis module 332. In further embodiments, detecting an interruption may include detecting skin freezing, monitoring treatment quality, identifying movement of the treatment device 104 (FIG. 1), as described in commonly assigned U.S. patent application Ser. No. 12/196,246 entitled "MONITORING THE COOLING OF SUBCUTANEOUS LIPID-RICH CELLS, SUCH AS THE COOLING OF ADIPOSE TISSUE," filed Aug. 21, 2008, the disclosure of which is incorporated by reference in its entirety.

A determination is made at stage 505. If an interruption is not detected, the process reverts to continuing the treatment process at stage 502. If an interruption is detected, the process continues to another stage 506 for determining with the analysis module 332 whether the treatment process may be resumed. The calculation module 336 may then determine the accumulated elapsed time of treatment and accumulate the elapsed time of interruption by, for example, activating another internal timer or counter. If the treatment process may not be resumed, the process reverts to initiating another treatment process at stage 502, and the calculation module 336 may reset both the elapsed time of treatment and the elapsed time of interruption.

If the treatment process is determined to be resumable, in one embodiment, the method 500 includes another stage 508 in which a recovery process is performed in response to the interruption. Optionally, in another embodiment, the interruption and the determination that the treatment process may be resumed can be indicated to the operator via, e.g., the display 118 (FIG. 1). The operator may choose to proceed with the recovery process or terminate the treatment process.

In one embodiment, performing the recovery process includes returning the adipose tissue to a condition (e.g., temperature) at least approximately equal to that at the time of the interruption. In other embodiments, if the interruption is detected based on tissue freezing, tissue overheating, and/or other suitable conditions, the adipose tissue may not be returned to a condition at least approximately equal to that at the time of interruption. Instead, performing the recovery process may include cooling, warming, and/or otherwise treating the adipose tissue and/or surrounding tissue based on suitable parameters to reduce the likelihood of injury. In yet other embodiments, performing the recovery process may include replacing the interface layer 220 with a new piece and pre-cooling the new interface layer 220 to a suitable temperature. Several embodiments of performing the recovery process are described in more detail below with reference to FIG. 6.

After performing the recovery process at stage 508, the method 500 may also include continuing the interrupted treatment process at stage 510. In one embodiment, continuing the interrupted treatment process includes performing the remaining treatment operations according to the treatment profile. For example, if the treatment profile includes cooling the skin 230 of the subject 101 for a total of 30 minutes, and the elapsed treatment time is 10 minutes, continuing the interrupted treatment process includes cooling the skin 230 of the subject 101 for another 20 minutes after performing the recovery process. In other embodiments, continuing the interrupted treatment process may also include performing other suitable operations according to the treatment profile.

Figure 6:
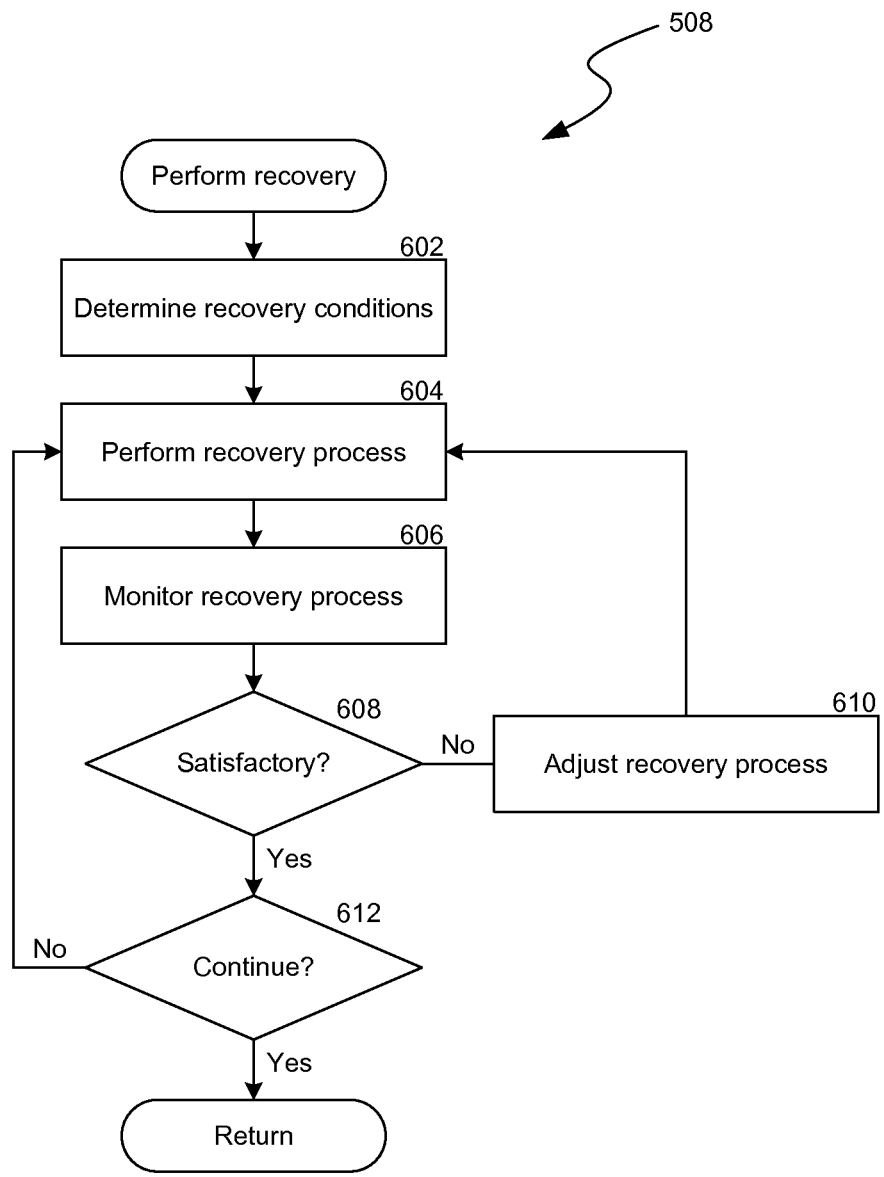
FIG. 6 is a flow diagram showing a method for performing a recovery process in accordance with embodiments of the invention.

FIG. 6 is a flow diagram showing a method 508 for performing a recovery process in accordance with embodiments of the invention. The method 508 may include determining recovery conditions (stage 602) with the calculation module 336 based on the elapsed time of treatment and the elapsed time of interruption. The recovery conditions may include a power level to the cooling plate 210 (FIG. 2), a recovery duration, an expected average rate of change of the interface temperature, and/or other suitable parameters.

Another stage 604 of the method 508 may include performing recovery via, e.g., cooling the adipose tissue according to the determined recovery conditions by, for example, activating the power supply 110 (FIG. 1) with the determined power level. In other examples, performing recovery may also include warming or a combination of cooling and warming the adipose tissue. In further examples, performing recovery may also include applying vibration, electrical stimulation, and/or other suitable procedures to the adipose tissue.

A further stage 606 of the method 508 may include monitoring the recovery process. For example, in one embodiment, monitoring the recovery process may include sensing the interface temperature with at least one of the temperature measurement components 217 and 227, converting the sensed interface temperature with the sensing module 330, and calculating a rate of change for the interface temperature with the calculation module 336. In other embodiments, monitoring the recovery process may include monitoring other suitable parameters.

The analysis module 332 may then determine whether the recovery process is satisfactory based on the calculated rate of change of the interface temperature and/or other suitable parameters at stage 608. If the recovery process is not satisfactory, another stage 610 of the method 508 includes adjusting the recovery process with the control module 334, and the process reverts to cooling the adipose tissue at stage 604. If the recovery process is satisfactory, another determination is performed at stage 612 to decide whether the process should return. In one embodiment, the determined recovery conditions include a recovery time, and if the recovery time has not expired, the process reverts to cooling the adipose tissue; otherwise, the process returns. In other embodiments, the operator and/or the subject 101 may terminate the recovery process.

Unless the context clearly requires otherwise, throughout the description and the claims, the words "comprise," "comprising," and the like are to be construed in an inclusive sense as opposed to an exclusive or exhaustive sense, that is to say, in a sense of "including, but not limited to." Words using the singular or plural number also include the plural or singular number, respectively. When the claims use the word "or" in reference to a list of two or more items, that word covers all of the following interpretations of the word: any of the items in the list, all of the items in the list, and any combination of the items in the list.

The various embodiments described above may be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entireties. Aspects of the invention may be modified, if necessary, to employ treatment devices and actuators with a plurality of treatment units, thermally conductive devices with various configurations, and concepts of the various patents, applications, and publications to provide yet further embodiments of the invention.

These and other changes may be made to the invention in light of the above-detailed description. In general, in the following claims, the terms used should not be construed to limit the invention to the specific embodiments disclosed in the specification and the claims, but should be construed to include all cooling that operates in accordance with the claims. Accordingly, the invention is not limited by the disclosure, but instead its scope is to be determined entirely by the following claims.

I claim:

1. A system for treating a subcutaneous lipid-rich region of a subject, comprising:
    a treatment device having a cooling plate configured to remove heat from the subcutaneous lipid-rich region of the subject during a treatment process; and
    a controller in electrical communication with the treatment device, the controller having a computer-readable medium containing instructions for performing a process comprising:
        performing a treatment process of the subcutaneous lipid-rich region with the treatment device to cool the subcutaneous lipid-rich region;
        detecting an interruption while the treatment device operates to cool the subcutaneous lipid-rich region during the treatment process;
        performing a recovery process in response to the detected interruption;
        returning the subcutaneous lipid-rich region of the subject to a condition generally similar to that at a time of the detected interruption; and
        continuing the treatment process to cool the subcutaneous lipid-rich region after performing the recovery process.

2. The system of claim 1 wherein the instructions for performing a recovery process further include instructions for performing a process comprising:
    determining an elapsed time of the treatment process;
    deriving an interrupt temperature ($T_{interrupt}$) of the subcutaneous lipid-rich region based on the elapsed time of the treatment process;
    determining an elapsed time of the interruption;
    deriving a rewarming temperature ($T_{rewarm}$) of the subcutaneous lipid-rich region based on the elapsed time of the interruption;
    calculating a cooling rate ($\dot{Q}$) for the recovery process as follows:

$$\dot{Q} = \frac{\rho V C_p (T_{rewarm} - T_{interrupt})}{\pi}$$

where $\rho$ is a density, V is a volume, and $C_p$ is a specific heat capacity of the subcutaneous lipid-rich region; and $\pi$ is a recovery duration;

initiating the recovery process by cooling the subcutaneous lipid-rich region according to the calculated cooling rate;

monitoring a rate of change in a temperature at an interface between the heat exchanging device and the subject; and if the monitored rate of change exceeds a threshold, adjusting the calculated cooling rate or the recovery duration based on the monitored rate of change.

3. The system of claim 1 wherein the instructions for performing a recovery process further include instructions for performing a process comprising:

determining an interrupt temperature ($T_{interrupt}$) of the subcutaneous lipid-rich region when the treatment process is interrupted;

determining a rewarming temperature ($T_{rewarm}$) of the subcutaneous lipid-rich region based on an elapsed time since the interruption;

calculating a cooling rate ($\dot{Q}$) for the recovery process as follows:

$$\dot{Q} = \frac{\rho V C_p (T_{rewarm} - T_{interrupt})}{\pi}$$

where $\rho$ is a density, V is a volume, and $C_p$ is a specific heat capacity of the subcutaneous lipid-rich region; and $\pi$ is a recovery duration.

4. The system of claim 1 wherein the instructions for performing a recovery process further include instructions for performing a process comprising:

determining whether the treatment process is resumable;

if the treatment process is resumable, performing the recovery process in response to the detected interruption; and if the treatment process is not resumable, initiating a new treatment process.

5. A controller useful for treating a subcutaneous lipid-rich region of a subject, the controller having a computer-readable medium containing instructions for performing a process comprising:

activating a cooling plate to remove heat from the subcutaneous lipid-rich region during a treatment process; and when the treatment process is interrupted while the cooling plate operates to cool the subcutaneous lipid-rich region, determining a profile for a recovery process to compensate for rewarming of the subcutaneous lipid-rich region of the subject during the interruption.

6. The controller of claim 5 wherein the profile for the recovery process includes at least one of an average cooling rate, a recovery duration, and an expected rate of change for a temperature at an interface between the subject and the cooling plate.

7. The controller of claim 5 wherein the profile for the recovery process includes an average cooling rate ($\dot{Q}$) and a recovery duration ($\pi$) related to each other as follows:

$$\dot{Q} = \frac{\rho V C_p (T_{rewarm} - T_{interrupt})}{\pi}$$

where $\rho$ is a density, V is a volume, and $C_p$ is a specific heat capacity of the subcutaneous lipid-rich region; $T_{rewarm}$ is a temperature of the subcutaneous lipid-rich region after the interruption; and $T_{interrupt}$ is a temperature of the subcutaneous lipid-rich region at the time of the interruption.

8. The controller of claim 5 wherein the profile for the recovery process includes an expected rate of change for a temperature at an interface between the subject and the cooling plate calculated as follows:

$$\Delta T = \frac{(T_{rewarm} - T_{interrupt})}{\pi}$$

where $T_{rewarm}$ is a temperature of the subcutaneous lipid-rich region after the interruption; $T_{interrupt}$ is a temperature of the subcutaneous lipid-rich region at the time of the interruption; and $\pi$ is a recovery duration.

9. The controller of claim 5 wherein the process further includes:

detecting the interruption in the treatment process;

determining whether the treatment process is resumable; and if the treatment process is resumable, performing the recovery process according to the determined profile and subsequently continuing the treatment process.

10. The controller of claim 5 wherein the profile for the recovery process includes an expected rate of change for a temperature at an interface between the subject and the cooling plate, and wherein the process further includes:

detecting the interruption in the treatment process;

determining whether the treatment process is resumable;

if the treatment process is resumable, and performing the recovery process according to the determined profile;

monitoring the rate of change; and adjusting the profile for the recovery process if the monitored rate of change deviates from the expected rate of change by a preselected amount.

11. The controller of claim 5 wherein the profile for the recovery process includes at least one of an average cooling rate, a recovery duration, and an expected rate of change for a temperature at an interface between the subject and the cooling plate, and wherein the process further includes:

detecting the interruption in the treatment process;

determining whether the treatment process is resumable; and if the treatment process is resumable, performing the recovery process according to the determined profile;

monitoring the rate of change for the temperature at the interface between the subject and the cooling plate; and if the monitored rate of change deviates from the expected rate of change by a preselected amount, performing at least one of increasing a power level to the heat exchanging device and increasing the recovery duration.

12. The controller of claim 5 wherein the process further includes determining an interruption temperature of the subcutaneous lipid-rich region at the time of the interruption and a rewarming temperature of the subcutaneous lipid-rich region after the interruption based on an elapsed time of the treatment process and an elapsed time of the interruption, respectively.

13. The controller of claim 5 wherein the process further includes a database containing lookup tables of temperatures of the subcutaneous lipid-rich region and corresponding cooling and/or rewarming durations, and wherein the process further includes determining an interruption temperature of the subcutaneous lipid-rich region at the time of the interruption and a rewarming temperature of the subcutaneous lipid-rich region after the interruption based on the lookup tables in the database and an elapsed time of the treatment process and an elapsed time of the interruption, respectively.

14. The system of claim 1 wherein the interruption is at least one of detaching of the treatment device from the subject and freezing of adipose tissue of the subject.

15. A system for treating a subcutaneous lipid-rich region of a subject, comprising:
   a treatment device configured to remove heat from the subcutaneous lipid-rich region of the subject during a treatment process; and
   a controller in communication with the treatment device and containing instructions for:
      starting a treatment process by removing heat from the subcutaneous lipid-rich region using the treatment device such that the subcutaneous lipid-rich region is substantially maintained within a treatment temperature range at which lipid rich cells in the subcutaneous lipid-rich region are affected;
      detecting an interruption of the treatment process before completion of the treatment process;
      performing a recovery process in response to the detected interruption, the recovery process including cooling the subcutaneous lipid-rich region to return the subcutaneous lipid-rich region to the treatment temperature range; and
      resuming the treatment process after performing the recovery process by substantially maintaining the subcutaneous lipid-rich region within the treatment temperature range to affect lipid rich cells in the subcutaneous lipid-rich region.

16. The system of claim 15 wherein performing the recovery process includes compensating for warming of the subcutaneous lipid-rich region of the subject after the interruption and before resuming the treatment process.

17. The system of claim 15 wherein the treatment temperature range is about −20° C. to about 20° C.

18. The system of claim 15 wherein performing the recovery process includes determining a profile for operating the treatment device to compensate for warming of the subcutaneous lipid-rich region of the subject to return the subcutaneous lipid-rich region to the treatment temperature range.

19. A system for treating a subcutaneous lipid-rich region of a subject, comprising:
   a treatment device configured to cool the subcutaneous lipid-rich region of the subject; and
   a controller in communication with the treatment device and containing instructions for:
      starting a treatment process by cooling the subcutaneous lipid-rich region using the treatment device such that the subcutaneous lipid-rich region is at a therapeutically effective cooled state;
      detecting an interruption of heat transfer between the treatment device and the subject before completion of the treatment process;
      after detecting the interruption, cooling the subcutaneous lipid-rich region such that the subcutaneous lipid-rich region is returned to the therapeutically effective cooled state; and
      after returning the subcutaneous lipid-rich region to the therapeutically effective cooled state, continuing the treatment process to substantially maintain the subcutaneous lipid-rich region at the therapeutically effective cooled state to complete the treatment process.

20. The system of claim 19 wherein continuing the treatment process to substantially maintain the subcutaneous lipid-rich region at the therapeutically effective cooled state includes maintaining the subcutaneous lipid-rich region within a temperature range of about −20° C. to about 20° C.

21. The system of claim 19 wherein controller further contains instructions for:
   determining whether the treatment process is resumable based on the detected interruption;
   if the treatment process is resumable, cooling the subcutaneous lipid-rich region to perform an uncompleted portion of the treatment process; and
   if the treatment process is not resumable, initiating a new protocol to complete the treatment process.

* * * * *